United States Patent [19]

Tsuchiya et al.

[11] Patent Number: 5,444,084

[45] Date of Patent: Aug. 22, 1995

[54] SUBSTITUTED HETEROCYCLIC DERIVATIVE HAVING SQUALENE EPOXIDASE INHIBITION ACTION AND ITS USE

[75] Inventors: Yoshimi Tsuchiya; Takashi Nomoto; Morihiro Mitsuya; Katsumasa Nonoshita; Masahiro Hayashi; Toshihiko Satoh; Yoshio Sawasaki; Toshio Kamei, all of Tsukuba, Japan

[73] Assignee: Banyu Pharmaceutical Co., Ltd., Tokyo, Japan

[21] Appl. No.: 190,065

[22] PCT Filed: May 28, 1993

[86] PCT No.: PCT/JP93/00723

§ 371 Date: Feb. 11, 1994

§ 102(e) Date: Feb. 11, 1994

[87] PCT Pub. No.: WO93/24478

PCT Pub. Date: Dec. 9, 1993

[30] Foreign Application Priority Data

Jan. 6, 1992 [JP] Japan ................................. 4-165393
Apr. 6, 1992 [JP] Japan ................................. 4-170122

[51] Int. Cl.$^6$ ................. C07D 333/16; C07D 333/18; A61K 31/38
[52] U.S. Cl. .................... 514/438; 514/444; 549/59; 549/60; 549/78; 549/80
[58] Field of Search ............ 549/78, 80, 59, 60; 514/438, 444

[56] References Cited

FOREIGN PATENT DOCUMENTS 0318860 11/1988 European Pat. Off. .
0448078 3/1991 European Pat. Off. .
50591988 6/1986 Japan .
31441989 6/1987 Japan .
905132 11/1988 WIPO .

OTHER PUBLICATIONS

Moore, et al., Am. Chem. Soc., (1992), 114:360–361, "Terminal Difluoro Olefin Analogues of Squalene Are Time–Dependent Inhibitors of . . . ".
Sen, et al., J. Med. Chem. (1989), 32:2152–2158, "Squalene Analogues Containing Isopropylidene Mimics as Potential Inhibitors of . . . ".
Mancuso, et al., J. Org. Chem. (1978), 43:2480–2482, "Oxidation of Long–Chain and Related Alcohols to Carbonyls by Dimethyl Sulfoxides . . . ".
Yamamoto, et al., J. Biol. Chem., (1970), 245:1670–1674, "Studies on Squalene Epoxidase of Rat Liver".
Ono, et al., J. Biol. Chem., (1975), 250:1571–1579, "Solubilization and Partial Characterization of Rat Liver Squalene Epoxidase".
"Agents Used to Treat Hyperlipidemia", Drug Evaluations, 6th Ed., 903–926 (1986).
Alberts, et al., Proc. Nat'l. Acad. Sci. USA (1980), 77:3957–3961.
Ceruti, et al. J. Chem. Res. (1988), 18–19, "Synthesis of Squalenoid Acetylenes and Allenes, as Inhibitors of Squalene Epoxidase".
Sen, et al., J. Am. Chem. Soc., (1989), 111:1508–1510, "Trisnorsqualene Alcohol, a Potent Inhibitor of Vertebrate Squalene Epoxidase".

*Primary Examiner*—Richard L. Raymond
*Assistant Examiner*—Mary C. Cebulak
*Attorney, Agent, or Firm*—Sherman and Shalloway

[57] ABSTRACT

Substituted heterocyclic derivatives represented by the formula (I)

$$R-Q^1-X-Y-Q^2\diagdown_C\diagup^{CH_2-Q^3-Q^4-\underset{R^4}{\overset{R^2}{\underset{|}{\overset{|}{C}}}}-R^3}_{C\diagdown R^1} \quad (1)$$

wherein R, $R^1$, $R^2$, $R^3$, $R^4$, $Q^1$, $Q^2$, $Q^3$, $Q^4$, X and Y are as defined, including, specifically, the compound (E)-3-[3-[3-(2-methoxymethyl-8,8-dimethyl-4-nonen-6-ynyl)phenoxymethyl]phenyl]thiophene, exhibit squalene epoxidase inhibiting activity and are useful in the treatment or prophylaxis of hypercholesterolemia, hyperlipidemia and arteriosclerosis.

10 Claims, No Drawings 5,444,084

SUBSTITUTED HETEROCYCLIC DERIVATIVE HAVING SQUALENE EPOXIDASE INHIBITION ACTION AND ITS USE

This application is a 371 of PCT/JP93/co723 filed May 20, 1993.

TECHNICAL FIELD

This invention relates to novel substituted heterocyclic derivatives, and more detailedly relates to substituted heterocyclic derivatives useful in the medicinal field, particularly in the field of treatment and prophylaxis of hypercholesterolemia, hyperlipidemia and further arteriosclerosis, and their use.

BACKGROUND ART

In recent years, it is pointed out that the occurrence frequency of arteriosclerosis and various diseases of coronary and encephalic arteries caused thereby is increasing due to increase of the rate of persons of advanced ages, changes of diet, etc. Various factors are considered for occurrence of this arteriosclerosis, and particularly, the increase of cholesterol in the blood is one of the most principal dangerous factors, and agents lowering cholesterol in the blood are effective for prophylaxis and treatment of arteriosclerosis [Agents Used to Treat Hyperlipidemia, Drug Evaluations 6th. edition, 903–926, (1986)]. Further, among these agents lowering cholesterol in the blood, agents inhibiting biosynthesis of cholesterol in the living body are highly rated because of their clear action mechanism and strong medicinal virtues [Proc. Natl. Acad. Sci., 77, 3957 (1980)]. However, since most of cholesterol biosynthesis-inhibiting agents so far known are inhibitors acting at the early stage or the late stage of the biosynthetic pathway, they have problems, for example, that they inhibit formation of other various physiologically important biological products simultaneously when they inhibit cholesterol biosynthesis, and further that accumulation of the precursors formed by the inhibition becomes a cause of other diseases.

The present inventors previously reported that a series of substituted alkylamine derivatives selectively inhibits squalene epoxidase located at the middle stage of the cholesterol biosynthesis system of mammals, and as a result are useful as an agent lowering cholesterol in the blood which has a mode of action different from that of known cholesterol biosynthesis-inhibiting agents (see Japanese Laid-Open Patent Publication No. 193746/1991, EP 0318860A2, WO 90/5132 and EP 0448078A2). Although several reports were made lately, besides the reports of the present inventors, on agents inhibiting squalene epoxidases of mammals, any of the disclosed compounds has only a low activity, and particularly, it is almost impossible to expect their effects on human beings, dogs, etc. [J. Chem. Research (s), 18–19 (1988); J. Am. Chem. Soc., 111, 1508–1510 (1989); ibid., 114, 360–361 (1992); J. Med. Chem., 32, 2152–2158 (1989); Japanese Laid-Open Patent Publication No. 3144/1989].

DISCLOSURE OF INVENTION

A main object of this invention is to provide an anti-hypercholesterolemia agent, an anti-hyperlipidemia agent and an agent for treatment and prophylaxis of arteriosclerosis each having higher safety and an excellent anti-cholesterol action, compared with known drugs.

As stated above, the present inventors previously reported that a series of substituted alkylamine derivatives selectively inhibits squalene epoxidases of mammals and at the same time has a strong anti-cholesterol action (see Japanese Laid-Open Patent Publication No. 93746/1991, EP 0318860A2, WO 90/5132 and EP 0448078A2).

As a result of further intense researches, the present inventors have, unexpectedly, found this time that substituted heterocyclic derivatives represented by the following general formula [I], which have no nitrogen atom so far considered to be essential for manifestation of activities, have further excellent characteristics, compared with the previously reported group of compounds.

Namely, accordingly to this invention, there is provided a substituted heterocyclic derivative represented by the general formula

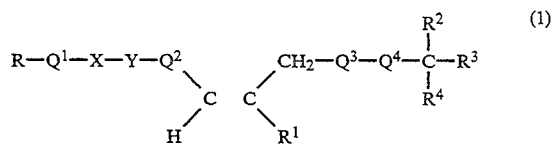

wherein R denotes a 5- or 6-membered heterocyclic group containing one or two hetero atoms selected from the group consisting of nitrogen atoms, oxygen atoms and sulfur atoms; $Q^1$ denotes a group represented by the formula

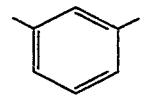

a group represented by the formula

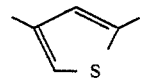

a group represented by the formula —CH═CH—CH$_2$—, a group represented by the formula —CH$_2$—CH═CH—, a group represented by the formula —CH$_2$—O—CH$_2$— or a trimethylene group; X and Y are the same or different and each represent a methylene group, an oxygen atom or a sulfur atom, or they combine to denote a vinylene group or an ethynylene group; $Q^2$ denotes (a) a 5- or 6-membered aromatic ring group represented by the formula

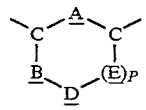

wherein A, B, D and E each denote a nitrogen atom, an oxygen atom, a sulfur atom or a group represented by the formula ═CH—, and p is an integer of 0 or 1, (b) a group represented by the formula —F—G—I— wherein F, G and I are the same or different, and each represent an oxygen atom, a sulfur atom, a methylene group or a group represented by the formula —CH=;

$R^1$ denotes a lower alkyl group, a lower alkenyl group, a lower hydroxyalkyl group, a lower alkoxyalkyl group, a lower alkanoyloxyalkyl group or a lower alkylthioalkyl group; . . . denotes a single bond or double bond provided that in the case of the single bond it is a group formed by addition of two hydrogen atoms to the corresponding double bond; $Q^3$ denotes an ethylene group, a vinylene group or an ethynylene group; $Q^4$ denotes a vinylene group or an ethynylene group; $R^2$ and $R^3$ are the same or different and denote lower alkyl groups, or they combine to denote a group forming a cycloalkane together with the adjacent carbon atom; and $R^4$ denotes a hydrogen atom, a lower alkyl group or a lower alkoxy group.

The compounds of the above general formula [I] in this invention inhibit squalene epoxidases of mammals extremely selectively and strongly, and are useful as pharmaceuticals for prophylaxis or treatment of hypercholesterolemia, hyperlipidemia, arteriosclerosis, etc.

Next, description is made on definitions and specific examples of various terms referred to in this description.

The term "lower" is used to mean that the number of carbon atoms of a group or compound modified with this term is 6 or less, preferably 5 or less.

Thus, as lower alkyl groups, there can be mentioned straight-chain or branched alkyl groups having 1 to 6, preferably 1 to 5 carbon atoms such as, for example, a methyl group, an ethyl group, a propyl group, an isopropyl group, a butyl group, an isobutyl group, a sec-butyl group, a tert-butyl group, a pentyl group, an isopentyl group, a neopentyl group and a hexyl group; as lower alkenyl groups, there can be mentioned straight-chain or branched alkenyl groups having 2 to 5 carbon atoms such as, for example, a vinyl group, a 1-propenyl group, an allyl group, a 2-methyl-1-propenyl group, a 2-methyl-2-propenyl group, a 1-butenyl group, a 2-butenyl group and a 1-pentenyl group; as lower hydroxyalkyl groups, there can be mentioned hydroxyalkyl groups of 1 to 5 carbon atoms having 1 or 2 hydroxyl groups such as, for example, a hydroxymethyl group, a 1-hydroxyethyl group, a 2-hydroxyethyl group, a 1-hydroxypropyl group, a 2-hydroxypropyl group, a 1-hydroxy-1-methylethyl group, a 2-hydroxy-1-methylethyl group, a 1-hydroxybutyl group, a 2-hydroxybutyl group, a 1-hydroxypentyl group, a 1,2-dihydroxyethyl group and a 1,2-dihydroxypropyl group; as lower alkoxyalkyl groups, there can be mentioned straight-chain or branched alkyl groups of 1 to 4 carbon atoms having a straight-chain or branched alkoxy groups of 1 to 3 carbon atoms such as, for example, a methoxymethyl group, an ethoxymethyl group, a propoxymethyl group, an isoproxymethyl group, a 1-methoxyethyl group, a 2-methoxyethyl group, a 1-methoxypropyl group, a 3-methoxypropyl group, a 1-methoxybutyl group, a 2-methoxy-1-methylethyl group, a 2-methoxy-2-methylethyl group and a 2-ethoxyethyl group; as lower alkanoyloxyalkyl groups, there can be mentioned straight-chain or branched alkyl groups of 1 to 4 carbon atoms having a straight-chain or branched alkanoyloxy group of 2 to 5 carbon atoms such as, for example, an acetoxymethyl group, a 1-acetoxyethyl group, a 2-acetoxyethyl group, a propanoyloxymethyl group and a pivaloyloxymethyl group; as lower alkylthioalkyl groups, there can be mentioned straight-chain or branched alkyl groups of 1 to 3 carbon atoms having a straight-chain or branched alkylthio group of 1 to 3 carbon atoms such as, for example, a methylthiomethyl group, an ethylthiomethyl group, a propylthiomethyl group, an isopropylthiomethyl group, a 1-methylthioethyl group, a 2-methylthioethyl group, a 1-methylthiopropyl group, a 3-methylthiopropyl group, a 1-methyl-2-methylthioethyl group and a 2-ethylthioethyl group; and as lower alkoxy groups, there can be mentioned straight-chain or branched alkoxy groups having 1 to 5 carbon atoms such as, for example, a methoxy group, an ethoxy group, a propoxy group, an isopropoxy group, a butoxy group, an isobutoxy group, a sec-butoxy group, a tert-butoxy group and a pentoxy group.

For further specific disclosure of the compounds of this invention represented by the above general formula [I], various symbols used in the formula [I] are further detailedly described enumerating their specific examples.

As the 5- or 6-membered heterocyclic group represented by R and containing one or two hetero atoms selected from the group consisting of nitrogen atoms, oxygen atoms and sulfur atoms, there can be mentioned an aromatic heterocyclic group such as, for example, a pyrrolyl group, a furyl group, a thienyl group, an oxazolyl group, an isoxazolyl group, a thiazolyl group, an isothiazolyl group, an imidazolyl group, a pyridyl group, a pyridazinyl group, a pyrimidinyl group or a pyrazinyl group; a non-aromatic heterocyclic group such as, for example, a dihydrothienyl group, a tetrahydrothienyl group, a pyrrolinyl group, a pyrrolidinyl group, an oxazolinyl group, an oxazolidinyl group, an isoxazolinyl group, an isoxazolidinyl group, a thiazolinyl group, a thiazolidinyl group, an isothiazolinyl group, an isothiazolidinyl group, a 1,2-dithiolanyl group, a 1,3-dithiolanyl group, a 1,2-dithiolyl group, a 1,3-dithiolyl group, a dihydrothiopyranyl group, a tetrahydrothiopyranyl group, a 1,4-dithianyl group, a 1,4-dithiinyl group, a 1,4-oxathiinyl group or a thiomorpholinyl group; or the like. Preferable among them are a thienyl group, a pyrrolyl group, an oxazolyl group, an isoxazolyl group, a thiazolyl group, an isothiazolyl group, an imidazolyl group, a pyridyl group, a dihydrothienyl group, etc., and further particularly preferable are a 3-thienyl group, a 1-pyrrolyl group, a 5-oxazolyl group, a 4-isoxazolyl group, a 5-isoxazolyl group, a 4-thiazolyl group, a 5-thiazolyl group, a 3-isothiazolyl group, a 4-isothiazolyl group, a 5-isothiazolyl group, a 3-pyridyl group, a 2,3-dihydro-4-thienyl group, a 2,5-dihydro-3-thienyl group, etc.

The group represented by $Q^1$ is a 1,3-substituted benzene

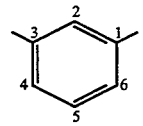

a 2,4-substituted thiophene

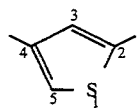

or a group represented by —CH=CHCH₂—, —CH₂CH=CH—, —CH₂OCH₂— or —(CH₂)₃—, and particularly preferable among them are 1,3-substituted benzenes, 2,4-substituted thiophenes and —CH=CHCH₂—.

Specific examples of the groups represented by X and Y are —CH₂CH₂—, —CH=CH—, —C≡C—, —CH₂O—, —OCH₂—, —CH₂S—, —SCH₂—, etc. formed by combination thereof, and —CH=CH—, —CH₂O— and —OCH₂— are particularly preferable.

Among the group Q², the aromatic ring (a) represented by the formula

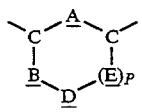

is a 5- or 6-membered aromatic ring optionally containing 1 to 3 hetero atoms selected from the group consisting of nitrogen atoms, oxygen atoms and sulfur atoms such as, specifically, a benzene ring, a pyrrole ring, a furan ring, a thiophene ring, an oxazole ring, an isoxazole ring, a thiazole ring, an isothiazole ring, an imidazole ring, a 1,3,4-oxadiazole ring, a 1,3,4,-thiadiazole ring, a pyridine ring, a pyridazine ring, a pyrimidine ring, a pyrazine ring or a triazine ring, and a benzene ring and a furan ring are particularly preferable. On the other hand, as examples of the group (b) represented by the formula —F—G—I—, there can be enumerated the following groups; —(CH₂)₃—, —CH=CHCH₂—, —CH₂CH=CH—, —OCH₂CH₂—, —CH₂OCH₂—, —CH₂CH₂O—, —SCH₂CH₂—, —CH₂SCH₂—, —CH₂CH₂S—, etc. Particularly preferable among these groups are —(CH₂)₃—, —CH=CHCH₂—, —CH₂CH=CH—, —CH₂OCH₂— and —CH₂SCH₂—.

R¹ denotes a lower alkyl group, a lower alkenyl group, a lower hydroxyalkyl group, a lower alkoxyalkyl group, a lower alkanoyloxyalkyl group or a lower alkylthioalkyl group, and among them, there can respectively be mentioned a methyl group, an ethyl group and a propyl group as preferred lower alkyl groups; a vinyl group, a 1-propenyl group and an allyl group as preferred alkenyl groups; a hydroxymethyl group, a 2-hydroxyethyl group and a 3-hydroxypropyl group as preferred lower hydroxyalkyl groups; a methoxymethyl group, an ethoxymethyl group and a 2-methoxyethyl group as preferred lower alkoxy alkyl groups; an acetoxymethyl group, a 2-acetoxyethyl group and a pivaloyloxymethyl group as preferred lower alkanoyloxyalkyl groups; and a methylthiomethyl group, an ethylthiomethyl group and a 2-methylthioethyl group as preferred lower alkylthioalkyl groups.

. . . denotes a single bond or double bond provided that the single bond is a group formed by addition of further two hydrogen atoms to the corresponding double bond. Therefore,

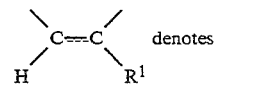

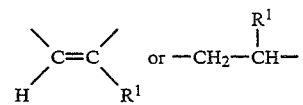

Q³ when denoted by the structural formula is —CH₂CH₂—, —CH=CH— or —C≡C—, and Q⁴ when denoted by the structural formula is —CH=CH— or —C≡C—, and trans (E) forms are preferable as geometrical isomers of the double bonds in these structural formulae.

R² and R³ are the same or different and lower alkyl groups, or they combine to denote a group forming a cycloalkane together with the adjacent carbon atom. Among them, as particularly preferred groups, there can be mentioned a case where R² and R³ each denote a methyl group or an ethyl group, or they form a cyclopropane ring together with the adjacent carbon atom (namely, the part represented by

is represented by

and further a case where both R² and R³ are methyl groups is particularly preferable.

R⁴ denotes a hydrogen atom, a lower alkyl group or a lower alkoxy group. As preferred lower alkyl groups, there can be mentioned straight-chain lower alkyl groups of 1 to 4 carbon-atoms such as, for example, a methyl group, an ethyl group, a propyl group and a butyl group, and as preferred lower alkoxy groups, there can be mentioned straight-chain alkoxy groups of 1 to 3 carbon atoms such as a methoxy group, an ethoxy group and a propoxy group. Among them, especially, a hydrogen atom, a methyl group, an ethyl group, a propyl group, a methoxy group, an ethoxy group and a propoxy group are preferable, and further a methyl group, an ethyl group, a methoxy group and an ethoxy group are particularly preferable.

Further, as to the compounds of the formula [I] of this invention, there is a case, depending on the forms of their substituents, where there exists a stereoisomer such as a diastereoisomer, a geometrical isomer or an optical isomer, and the compounds of the formula [I] of this invention include all these stereoisomers and their mixtures.

Next, description is made on processes for preparation of the compounds according to this invention.

The compounds of the formula [I] of this invention can, for example, be prepared according to the processes shown in the following reaction formulae 1 to 6.

Reaction formula 1
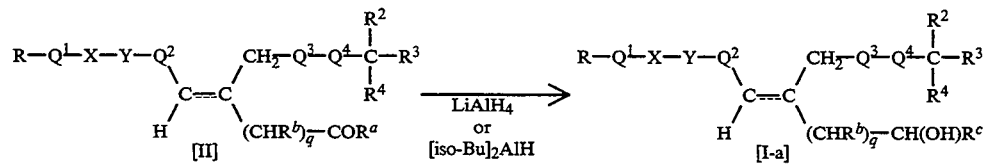
Reaction formula 2
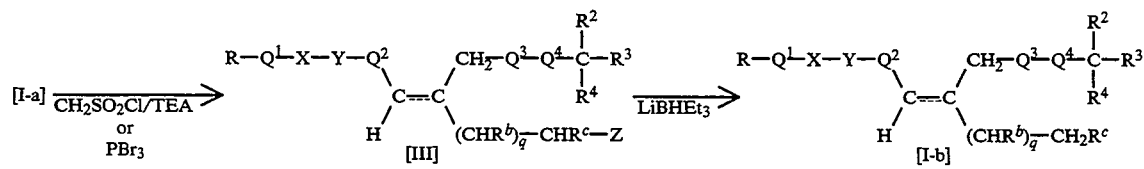
Reaction formula 3
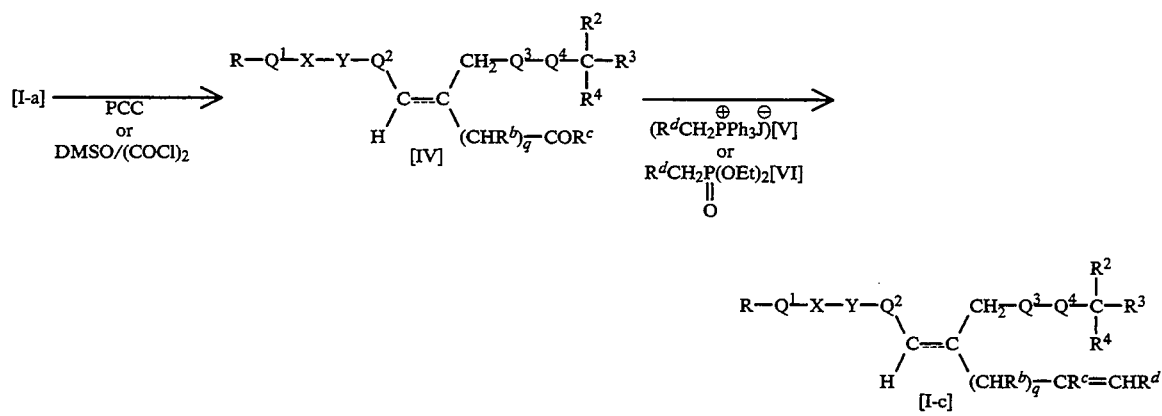
Reaction formula 4
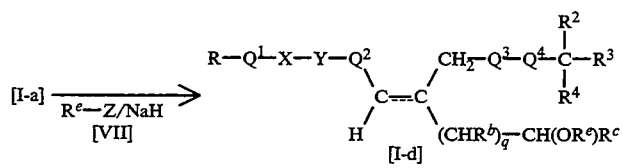
Reaction formula 5
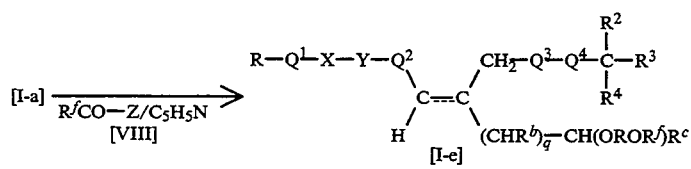
Reaction formula 6
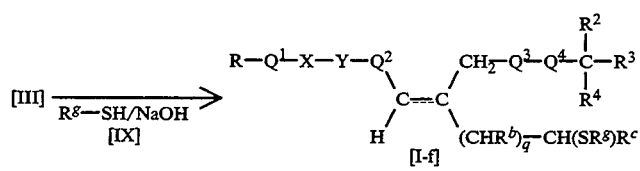
Reaction formula 7

-continued

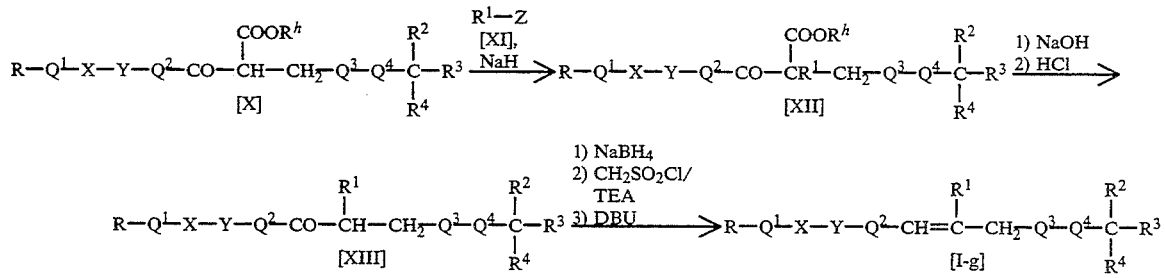

wherein Z denotes a leaving group, $R^a$ denotes a lower alkoxy group or a lower alkyl group, $R^b$, $R^c$ and $R^d$ denote hydrogen atoms or lower alkyl groups, $R^e$, $R^f$, $R^g$ and $R^h$ denote lower alkyl groups, q denotes an integer of 0, 1 or 2, J denotes a halogen atom, and R, $Q^1$, X, Y, $Q^2$, $Q^3$, $Q^4$, $R^2$, $R^3$ and $R^4$ have the aforesaid meanings.

Among the above formulae, as the eliminatable group represented by Z, there can, specifically, be mentioned a halogen atom such as, for example, a chlorine atom, a bromine atom or an iodine atom, an organic sulfonyloxy group such as a methanesulfonyloxy group or a p-toluenesulfonyloxy group, or the like. Further, there can respectively be mentioned, for example, as lower alkoxy groups represented by $R^a$ a methoxy group, an ethoxy group, etc., and as lower alkyl groups represented by $R^a$ a methyl group, an ethyl group, a propyl group, an isopropyl group, etc.; as lower alkyl groups represented by $R^b$ a methyl group, etc.; as lower alkyl groups represented by $R^c$ a methyl group, an ethyl group, a propyl group, an isopropyl group, etc.; as lower alkyl groups represented by $R^d$ a methyl group, an ethyl group, etc.; as lower alkyl groups represented by $R^e$ a methyl group, an ethyl group, etc.; as lower alkyl groups represented by $R^f$ a methyl group, an ethyl group, a propyl group, an isopropyl group and a tert-butyl group; as lower alkyl groups represented by $R^g$ a methyl group, an ethyl group, a propyl group, an isopropyl group, etc.; further as lower alkyl groups represented by $R^h$ a methyl group, an ethyl group, etc.

All the reactions represented by the above Reaction formulae 1 to 7 are applied examples of reactions well known in the field of organic synthetic chemistry, and it is possible to select various reaction conditions taking the physical properties of raw material compounds into consideration.

Specific reaction examples usable for preparation of the compounds [I] of this invention are enumerated below, but it is a matter of course that synthetic processes of the compounds [I] of this invention are not limited to these reaction examples.

Reaction formula 1 relates to preparation of alcohol derivatives [I-a] having a hydroxyl group in $R^1$ in the formula of the compounds of this invention represented by the general formula [I]. According to this invention, such an alcohol compound can be prepared by making a reducing agent such as a metal hydride complex act on a carboxylic acid ester derivative or ketone derivative represented by the general formula [II] in a solvent having no bad influence on the reaction. There can preferably be used as solvents ethers such as, for example, ethyl ether and tetrahydrofuran, halogenated hydrocarbons such as, for example, methylene chloride and chloroform, aromatic hydrocarbons such as, for example, benzene and toluene, and alcohols such as, for example, methanol and ethanol, and as reducing agents metal hydride complexes such as lithium aluminum hydride (LiAlH$_4$), diisobutylaluminum hydride ([iso-Bu]$_2$AlH) and sodium borohydride (NaBH$_4$). Further, as specific reaction conditions, there are, for example, a process which comprises dissolving a compound [II] in an ethereal solvent such as tetrahydrofuran, and carrying out reaction at 0° C. to room temperature for 1 to 6 hours using, preferably, lithium aluminum hydride in an amount equimolar or excess-molar to the compound [I].

Reaction formula 2 relates to preparation of compounds [I-b] such that $R^1$ in the general formula [I] of the compounds of this invention is a lower alkyl group. According to this invention, such a compound [I-b] can, for example, be prepared by converting the hydroxyl group of an alcohol compound [I-a] obtained above as a raw material to a leaving group, and then making a reducing agent such as a metal hydride complex act thereon in a solvent having no bad influence on the reaction. In the reaction, there can be used, as solvents, solvents exemplified in the above Reaction formula 1 as such, and as reducing agents, there can be used lithium triethylborohydride (LiBHEt$_3$) so-called super hydride, etc. besides metal hydride complexes enumerated in Reaction formula 1. Further, the conversion of the hydroxyl group of the alcohol compound [I-a] to the leaving group can be accomplished by using as a solvent, for example, an ester such as ethyl acetate, a halogenated hydrocarbon such as methylene chloride or chloroform, an aromatic hydrocarbon such as benzene or toluene, or an ether such as ethyl ether or tetrahydrofuran, either making a sulfonylating agent such as methanesulfonyl chloride (CH$_3$SO$_2$Cl) or p-toluenesulfonyl chloride act thereon in the presence of a base such as triethylamine (TEA) or pyridine (C$_5$H$_5$N), or making a halogenating agent such as phosphorus tribromide (PBr$_3$) or thionyl chloride act thereon in the presence of a base as mentioned above. As more specific reaction conditions, there are, for example, a process which comprises dissolving a compound [I-a] in ethyl acetate, adding methanesulfonyl chloride and triethylamine each in an amount equimolar to small-excess molar to the compound [I-a], carrying out reaction at 0° C. to room temperature for 1 to 6 hours to obtain a compound [III] wherein a leaving group (a methanesulfonyloxy group) was introduced, then dissolving the compound in an ethereal solvent such as tetrahydrofuran, adding preferably a 2 to 10 equivalent amount of lithium triethylborohydride, and carrying out reaction at 0° C. to room temperature for 1 to 6 hours.

Reaction formula 3 relates to preparation of compounds [I-c] having a double bond in the substituent $R^1$ in the general formula [I] of the compounds of this invention. According to this invention, such a compound [I-c] can, for example, be prepared by using an alcohol compound [I-a] obtained in the above as a raw material, converting it to a corresponding ketone or aldehyde compound [IV] using an oxidizing agent, and making a phosphonium salt or phosphonate represented by the general formula [V] or [VI], a so-called Wittig reagent act thereon, in a solvent having no bad influence on the reaction. In this reaction, as solvents, there can preferably be used tetrahydrofuran, dimethylformamide, etc. in the case of phosphonium salt derivatives [V], and tetrahydrofuran, benzene, toluene, etc. in the case of the phosphonate derivatives. Further, it is preferable to carry out this reaction usually in the presence of a base, and particularly when a phosphonium salt derivative is used as a raw material, it is necessary to make the base act thereon in advance or in the reaction system. As examples of the base, there can be mentioned sodium hydroxide, sodium hydride, butyl lithium, etc. Further, the oxidation reaction of the alcohol compound [I-a] to the ketone compound or aldehyde compound [IV], pre-stage reaction, can, for example, be carried out, in a halogenated hydrocarbon such as methylene chloride or chloroform, by using pyridium chlorochromate (PCC) or pyridium dichromate, or by the process disclosed in J. Org. Chem., 43, 2481 (1978) wherein oxalyl chloride ($(COCl)_2$) and dimethyl sulfoxide (DMSO) are used. As more specific reaction conditions of these reactions, there are, for example, a process which comprises dissolving a compound [I-a] in methylene chloride, adding dropwise this solution to a methylene chloride solution of an oxidizing agent prepared in advance from oxalyl chloride and dimethyl sulfoxide each in an 1 to 5 equivalent amount to the compound [I-a], adding a 1 to 10 equivalent amount of triethylamine, carrying out reaction at $-80°$ to $0°$ C. for 5 minutes to 3 hours to give a ketone compound or aldehyde compound [IV], adding a tetrahydrofuran solution of this compound to a tetrahydrofuran solution of a Wittig reagent prepared in advance from a phosphonium salt derivative [V] in an amount equimolar to small excess-molar to the compound [IV] and a solution of n-butyl lithium in hexane, and carrying out reaction at $-70°$ C. to room temperature for 30 minutes to 24 hours.

Reaction formula 4 relates to preparation of compounds [I-d] wherein $R^1$ in the general formula [I] of the compounds of this invention is a lower alkoxyalkyl group. According to this invention, such a compound [I-d] can, for example, be prepared by reacting an alcohol compound [I-a] obtained in the above as a raw material with an alkylating agent [VII], in the presence of a base, in a solvent having no bad influence on the reaction. In this reaction, there can preferably be used as the alkylating agent [VII] an alkyl halide or alkyl sulfate ester having a corresponding alkyl group, and as the solvent, for example, an ether such as ethyl ether or tetrahydrofuran, dimethylformamide, or the like. Further, as bases used in the reaction, metal sodium, metal potassium, sodium hydride, butyl lithium, etc. are preferable. Further, as more specific reaction conditions of this reaction, there are, for example, a process which comprises dissolving an alcohol compound of a compound [I-a] in tetrahydrofuran, making sodium hydride act thereon at $-20°$ C. to room temperature for 10 minutes to 2 hours to prepare an alcoholate, adding an alkylating agent [VII] to this solution, and carrying out reaction at $-20°$ to $100°$ C. for 1 to 24 hours. Further, a desired compound [I-d] can also be prepared by using as a raw material a leaving-group-containing compound [III] used in Reaction formula 2, and making a metal alkoxide of a corresponding lower alkanol act thereon.

Reaction formula 5 relates to preparation of compounds [I-e] wherein the substituent $R^1$ of the general formula [I] of the compounds of this invention is a lower alkanoyloxyalkyl group. According to this invention, such a compound [I-e] can, for example, be prepared by making acylating agent [VIII] act on an alcohol compound [I-a] obtained in the above, in the presence of a base, in a solvent having no bad influence on the reaction. In this reaction, as the acylating agent [VIII], there can preferably be used an acid halide or acid anhydride or the like of a corresponding aliphatic saturated carboxylic acid, and as the solvent, there can preferably be used, for example, a halogenated hydrocarbon such as methylene chloride or chloroform, an aromatic hydrocarbon such as benzene or toluene, or an ether such as ethyl ether or tetrahydrofuran. Further, as the base, there can preferably be used an inorganic base such as sodium hydroxide, potassium hydroxide, sodium carbonate, potassium carbonate or sodium bicarbonate, or an organic base such as pyridine, 4-dimethylaminopyridine or triethylamine. As more specific reaction conditions of this reaction, there are, for example, a process which comprises dissolving an alcohol compound of a compound [I-a] in a halogenated hydrocarbon solvent such as methylene chloride, adding a base and an acylating agent [III] each in an amount equimolar or small excess-molar to the compound [I-a], and carrying out reaction at $0°$ C. to room temperature for 1 to 6 hours.

Reaction formula 6 relates to preparation of compounds [I-f] wherein the substituent $R^1$ of the general formula [I] of the compounds of this invention is a lower alkylthioalkyl group. According to this invention, such a compound [I-f] can, for example, be prepared by reacting a leaving group-containing derivative [III] obtained in the above as a raw material with a corresponding alkylmercaptan [IX], in the presence of a base, in a solvent having no bad influence on the reaction. In the reaction, as the solvent, there can preferably by used an alcohol such as methanol or ethanol, a halogenated hydrocarbon such as methylene chloride or chloroform, an ether such as tetrahydrofuran or dioxane, dimethylformamide, or the like, and as the base, there can preferably be used an inorganic base such as sodium hydroxide, potassium hydroxide, sodium carbonate or potassium carbonate, or an organic base such as pyridine or triethylamine. Further, as specific reaction conditions of this reaction, there are, for example, a process which comprises dissolving a leaving group-containing derivative [III] in an alcohol solvent such as methanol or ethanol, adding a base and an alkylmercaptan [IX] or a sodium salt of the alkylmercaptan each in an amount equimolar or excess-molar to the compound [III], and carrying out reaction at $0°$ C. to room temperature for 1 to 6 hours.

Reaction formula 7 is one of general synthetic processes for compounds wherein the part represented by . . . in the formula of the compounds [I] of this invention is a double bond, and is applicable to many compounds. According to this invention, a compound [I] can, for example, be prepared by making act on a β-keto-acid derivative represented by the general formula [X] a corresponding alkylating agent [XI] to obtain an alkyl compound [XII], subjecting it to hydrolysis of the ester group and subsequent decarboxylation, reducing a ketone compound [XIII] obtained by these steps to an alcohol compound, converting the formed hydroxyl group to a leaving group, and treating the resultant compound with a base. A series of these steps is more specifically described below mentioning examples of preferred reaction conditions. The alkylation reaction, the first step, can, for example, be carried out by making an alkylating agent in an amount equimolar or excess-molar to the raw material β-keto acid [X] act on the β-keto acid at −20° to 100° C. for 1 to 24 hours, in the presence of a base such as, for example, sodium hydride or potassium tert-butoxide, in a solvent not participating in the reaction such as, for example, tetrahydrofuran, ethyl ether, benzene or dimethylformamide. The next steps of hydrolysis and decarboxylation of the ester group can, for example, be carried out by treating the resultant alkyl compound [XII], at room temperature to 100° C. for 1 to 24 hours, with a base such as sodium hydroxide or potassium hydroxide in an amount of equimolar or excess-molar to the alkyl compound in an alcoholic solvent such as methanol or ethanol, and then heating the resultant carboxylic acid in an acidic condition at 50° to 150° C. for 1 to 24 hours. Further, the conversion of the ketone compound [XIII] to the desired compound [I] can, for example, be carried out by making a reducing agent such as a metal hydride complex act on the ketone compound [XIII] in a solvent having no bad influence on the reaction to reduce the ketone compound to an alcohol compound, converting the hydroxyl group of the resultant alcohol compound to a leaving group such as a halogen atom or an organic sulfonyloxy group, and heating the resultant compound at 50° to 200° C. for 1 to 48 hours in the presence of a base such as 1,8-diazabicyclo[5.4.0]-7-undecene (DBU) in an amount equimolar or excess-molar to the raw material compound in a high boiling aromatic hydrocarbon solvent such as, for example, toluene or xylene. In the steps, in the above reactions, of reduction of the ketone compound [XIII] to the alcohol compound and conversion of the hydroxyl group of the alcohol compound to the leaving group, the reduction conditions and the conditions for introduction of leaving groups used respectively in the above Reaction formula 1 and Reaction formula 2 can be utilized as such.

Compounds [I] of this invention obtained in the above steps can be isolated and purified, for example, by utilizing column chromatography, solvent extraction, recrystallization, etc. solely or in appropriate combination.

Raw material compounds used in the above Reaction formulae 1 to 7 and represented by the general formulae [II], [IV] and [X] can be prepared through various steps according to various preparation processes known in organic synthetic chemistry, because of variety of their structures. Among these preparation processes, there are, for example, the following processes disclosed in the later-described Reference Examples by the present inventors.

(Preparation process 1)

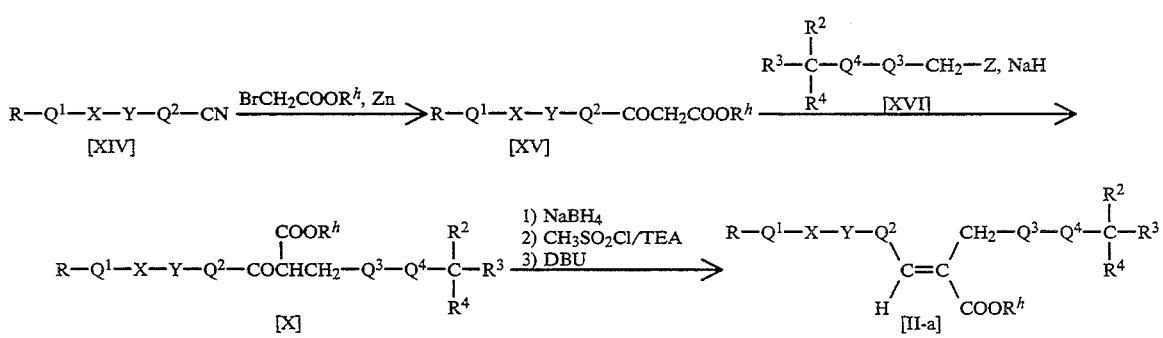

(Preparation process 2)

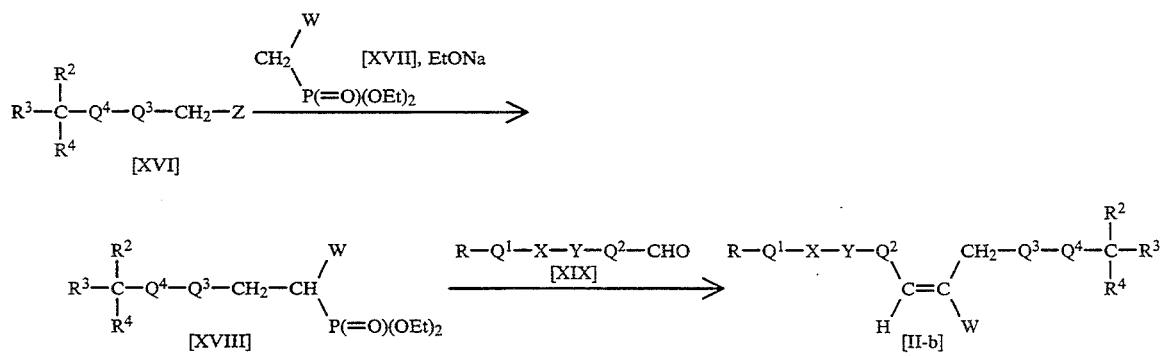

(Preparation process 3)

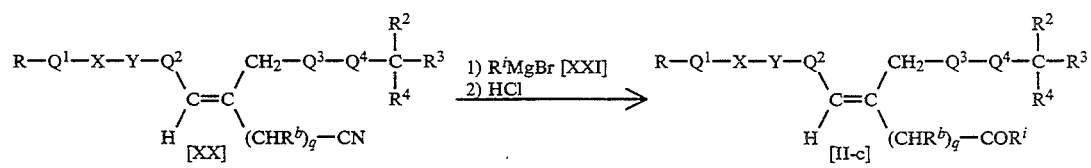

-continued (Preparation process 4)

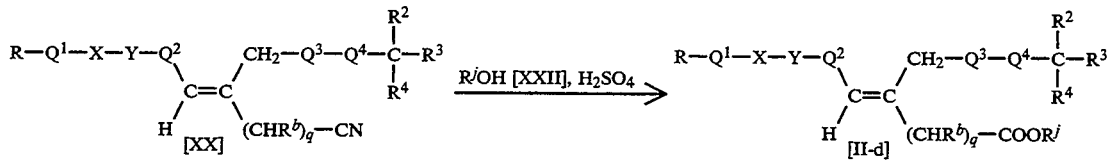

(Preparation process 5)

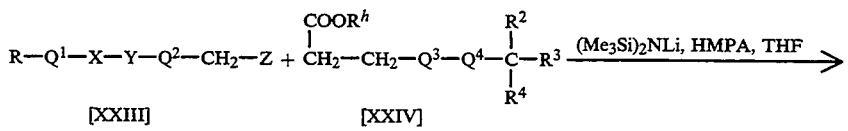

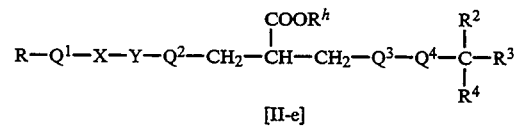

(Preparation process 6)

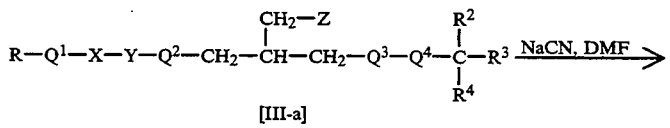

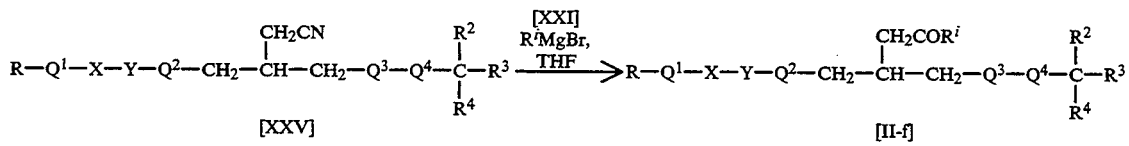

wherein $R^i$ and $R^j$ denote lower alkyl groups, W denotes a cyano group or a lower alkoxycarbonyl group, and R, $Q^1$, $Q^2$, $Q^3$, $Q^4$, $R^2$, $R^3$, $R^4$, $R^b$, $R^h$, Z and q have the aforesaid meanings.

Further, raw material compounds of the formulae [V], [VI], [VII], [VIII], [IX], [X], [XI], [XIV], [XVI], [XVII], [XIX], [XX], [XXI], [XXII], [XXIII] and [XXIV] can be purchased as commercial products, or prepared by preparation processes disclosed in Japanese Laid-Open Patent Publication No. 5059/1988, preparation processes previously reported by the present inventors (see Japanese Laid-Open Patent Publication No. 193746/1991, EP 18860A2, WO 90/5132 and EP 0448078A2) or processes similar to them, and further preparation processes disclosed in the later-described Referential Examples, etc.

The compounds of the formula [I] of this invention have only low toxicity, and inhibit squalene epoxidase extremely selectively and strongly in the living body of mammals, and therefore are useful compounds whose uses as an anti-hypercholesterolemia agent, an anti-hyperlipidemia and further an anti-arteriosclerosis agent are expected.

For verifying this, description is made below according to test examples.

Pharmacological test example 1

Squalene epoxidase inhibition action (1) Preparation of squalene epoxidase

Human squalene epoxidase is prepared in accordance with the process disclosed in J. Biol. Chem., 245, 1670 (1970); ibid., 250, 1572 (1975).

Namely, human hepatoma (Hep-G2) cells are cultured at 37° C. under air containing 5% carbon dioxide. After completion of the culture, the cells are scraped and collected by centrifugation. The cells are suspended in 0.1M Tris-HCl buffer (pH 7.5) ($1 \times 10^8$ cells/ml), the suspension is homogenized and centrifuged at 9750 Xg for 10 minutes, and then the sediment is washed with 0.1M Tris-HCl buffer (pH 7.5) and centrifuged at 105,000 Xg for 1 hour. The resultant microsome is suspended in 0.1M Tris-HCl buffer (pH 7.5) so that the protein amount becomes 20 mg/ml, and solubilized by stirring the suspension under ice cooling in the presence of 1% Triton X-100. After this solubilization treatment, the concentration of Triton X-100 is diluted to 0.125% with 1 mM EDTA and 1 mM dithiothreitol, and the dilution is centrifuged at 105,000 Xg for 1 hour. The resultant supernatant is used as the squalene epoxidase fraction in the later-described test.

(2) Assay of squalene epoxidase activity

Assay of human squalene epoxidase activity is carried out according to the method disclosed in J. Biol. Chem., 245, 1670 (1970).

Namely, 3 μl of a dimethyl sulfoxide solution of a test chemical is added to a solution consisting of 0.2 ml of the squalene epoxidase fraction [protein amount 0.4 mg, 0.1% Triton X-100, 20 μM Tris-HCl buffer (pH 7.5)] prepared in (1), 100 μM FAD, 1 mM NADPH, 1 mM EDTA and 8 μM $^3$H-squalene-Tween 80 suspension to make the total volume 0.3 ml, and the mixture is subjected to reaction with shaking at 37° C. for 60 minutes. 0.3 ml of 10% potassium hydroxide-methanol solution is added to discontinue the reaction, and the mixture is heated at 75° C. for 1 hour. Then the non-saponified substance is extracted with petroleum ether and the extract is concentrated to dryness under a nitrogen stream. The resultant residue is dissolved in a small amount of ethyl ether, pre-coated Silicagel TCL is spotted with the extract, and development is carried out with benzeneethyl acetate (99.5:0.5). The position of the $^3$H-squalene-2,3-epoxide in the TLC is confirmed using ergosterol acetate as a marker, and the $^3$H-squalene-2,3-epoxide portion in the TLC is cut out. The TLC piece is immersed in a toluene series scintillator and measurement is made using a liquid scintillation counter. Thereby, the inhibition rates (%) against squalene epoxidase at 3 μM concentration of compounds of this invention are determined, and the results are shown in the following Table 1.

TABLE 1

| Human squalene epoxidase inhibition action | |
|---|---|
| Test chemical | Inhibition rate at 3 μM concentration |
| Compound of Example 1 | 100% |
| Compound of Example 2 | 100% |
| Compound of Example 4 | 100% |
| Compound of Example 5 | 100% |
| Compound of Example 6 | 100% |
| Compound of Example 8 | 100% |
| Compound of Example 10 | 100% |
| Compound of Example 11 | 88% |
| Compound of Example 12 | 100% |
| Compound of Example 18 | 99% |
| Compound of Example 21 | 100% |
| Compound of Example 22 | 100% |
| Compound of Example 23 | 100% |
| Compound of Example 29 | 100% |
| Compound of Example 30 | 100% |
| Compound of Example 32 | 100% |
| Compound of Example 33 | 100% |
| Compound of Example 34 | 100% |
| Compound of Example 38 | 100% |
| Compound of Example 42 | 100% |
| Compound of Example 43 | 100% |
| Compound of Example 44 | 100% |

Pharmacological test example 2

Inhibition test of in vivo cholesterol biosynthesis

In this in vivo test, female SD rats (5 weeks old) are used. The rats are raised for 9 days under an environment where illumination is applied with reversed day and night (dark from 6 a.m. to 6 p.m.), and meanwhile they can freely ingest a solid feed and water. A test chemical is orally administered two hours before dark 6 o'clock when cholesterol biosynthesis becomes maximum. The compound is dissolved in a middle-chain fatty acid triglyceride, and orally administered at 3 mg/kg in an amount of 0.5 ml/100 g body weight. Further, the same volume of the solvent (vehicle) used is administered to control animals. Five hours after the administration of the test chemical, 20μ Ci/100 g body weight of $^{14}$C-sodium acetate (56 m Ci/m mole) is intraperitoneally administered to the rats, respectively. At dark 6 o'clock blood is sampled from the abdominal artery of each animal under ether anesthesia and centrifuged to separate the plasma.

2 ml of 15% potassium hydroxide-methanol solution is added per ml of the plasma, and the mixture is heated at 75° C. for 3 hours to carry out saponification. Each sample is extracted twice, each time with 2 ml of petroleum ether, and the extract is washed with 2 ml of distilled water. Finally each extract is evaporated to dryness under a nitrogen stream.

The resultant residue is dissolved in a small amount of ethyl ether, and a pre-coated silica gel TLC is spotted with the total amount of the solution. This plate is developed with a solvent system of hexane/ethyl ether/acetic acid (85:15:4). Coloring is carried out with iodine, and radioactivity at the cholesterol part is assayed using a liquid scintillation counter.

The results (Table 2) are expressed by dpm values of produced $^{14}$C-cholesterol existing in 1 ml of each plasma. Further, the inhibition of cholesterol biosynthesis is calculated by comparing the amounts of $^{14}$C-cholesterol biosynthesis between the test groups and the control group.

TABLE 2

| Cholesterol biosynthesis inhibition test (n = 5) in rat | | |
|---|---|---|
| Test chemical | $^{14}$C-cholesterol, dpm (control) | Cholesterol biosynthesis inhibition rate |
| Compound of Example 1 | 275 (3092) | 91% |
| Compound of Example 6 | 871 (3218) | 73% |
| Compound of Example 12 | 1208 (3092) | 61% |
| Compound of Example 34 | 347 (2282) | 85% |
| Compound of Example 38 | 350 (2282) | 85% |

Subacute toxicity test example

The compound of Example 34 was suspended in 0.5% aqueous methylcellulose solution and orally administered to groups of rats (SD male), each group consisting of 3 animals, at a rate of 300 mg/kg per day for 7 days. As a result, death and other toxic symptoms were not observed at all.

As apparent from the above results, the compounds of this invention inhibit squalene epoxidase strongly and inhibit the biosynthesis of cholesterol, and are thus effective for treatment and prophylaxis of various diseases caused, for example, by exacerbation of the cholesterol biosynthesis system and/or excessive intake of cholesterol, for example diseases such as obesity, hypercholesterolemia, hyperlipidemia and arteriosclerosis. Further, the squalene epoxidase inhibition action of the compounds of this invention does not work on fungi and is specific for mammals and their toxicity is extremely low and thus this invention is very useful in the medicinal field.

The compounds of the formula [I] of this invention can be administered orally or parenterally, and can be provided for treatment and prophylaxis of hypercholesterolemia, hyperlipidemia and arteriosclerosis, etc. after formulation into forms suited for such administration. In clinical use of the compounds of this invention, it is also possible to make administration after various formulations by addition of pharmacologically acceptable additives in accordance with their administrational forms. As such additives, various additives usually used in the pharmaceutical field can be used, and there can, for example, be mentioned gelatin, lactose, saccharose, titanium oxide, starches, crystalline cellulose, hydroxypropylmethylcellulose, carboxymethylcellulose, corn starch, microcrystalline waxes, white petrolatum, magnesium metasilicate aluminate, anhydrous calcium phosphate, citric acid, trisodium citrate, hydroxypropylcellulose, sorbitol, sorbitan fatty acid esters, polysorbates, sucrose fatty acid esters, polyoxyethylene-hardened castor oil, polyvinylpyrrolidone, magnesium stearate, light silicic anhydride, talc, vegetable oils, benzyl alcohol, gum arabic, propylene glycol, polyalkylene glycol, cyclodextrin, hydroxypropylcyclodextrin, etc.

As dosage forms into which the compounds of this invention are formulated as mixtures with these additives, there are solid preparations such as, for example, tablets, capsules, granules, powders and suppositories and liquid preparations such as, for example, syrups, elixirs and injections, and these can be prepared according to usual processes in the pharmaceutical field. In liquid preparations, it is also possible to adopt forms such that they are dissolved or suspended in water or other appropriate solvents at the time of use. Further, particularly in the case of injections, it is also possible to dissolve or suspend the compounds of this invention, if necessary, in physiological saline or a glucose solution, and it is further possible to add buffers and preservatives.

Such a preparation can contain a compound of this invention at a rate of 1.0 to 100 wt. %, preferably 1.0 to 60 wt. % of the whole preparation. Such a preparation can also contain other therapeutically effective compounds.

When a compound of this invention is used as an anti-hyperlipidemia agent, an anti-arteriosclerosis agent or an anti-hypercholesterolemia agent, its administration amount and administration frequency vary depending on the distinction of sex, age, weight, the extent of the symptom of patients, and the kind and scope of desired therapeutic effects, etc., but is generally preferable in the case of oral administration to administer the compound in an amount of 0.01 to 20 mg/kg to an adult once a day or several times a day in a divided form, and in the case of parenteral administration to administer it in an amount of 0.001 to 2 mg/kg to an adult once a day or several times a day in a divided form.

This invention is described more specifically below according to examples, but it is a matter of course that this invention is not limited to these examples.

EXAMPLE 1

Preparation
(E,E,E))-2-(6,6-dimethyl-2-hepten-4-ynyl)-8-[3-(3-thienyl)phenyl]-2,7-octadien-1-ol 260 mg of (E,E,E)-2-(6,6-dimethyl-2-hepten-4-ynyl)-8-[3-(3-thienyl)phenyl]-2,7-octadienic acid methyl ester is dissolved in 10 ml of methylene chloride. 1.5 ml of 1M toluene solution of diisobutylaluminum hydride is added thereto under cooling at −78° C. and stirring and the mixture is stirred at that temperature for 1.5 hours. Saturated aqueous solution of Rochelle salt and methylene chloride are added to the reaction solution to form two liquid phases, the organic layer is taken and dried over anhydrous magnesium sulfate, and then the solvent is distilled off under reduced pressure. The residue is purified by silica gel column chromatography [Wako gel C-100, 30 g; hexane/ethyl acetate=4/1] to obtain 230 mg (yield: 95%) of the captioned compound as a colorless oily matter.

NMR (CDCl$_3$) δ:1.22 (9H, s), 1.50–1.64 (2H, m), 2.11 (2H, q, J=7.2Hz), 2.25 (2H, q, J=6.6Hz), 2.89 (2H, br.d, J=6.6Hz), 4.03 (2H, d, J=5.2Hz), 5.50 (1H, dt, J=15.8Hz, 1.6Hz), 5.51–5.59 (1H, m), 5.99 (1H, dt, J=15.8 Hz, 6.6Hz), 6.36 (1H, dt, J=15.8Hz, 6.6Hz), 6.44 (1H, d, J=15.8Hz), 7.22–7.49 (6H, m), 7.55 (1H, br.s)

The alcohol derivatives of Examples 2 to 10 are obtained by carrying out the same reaction as in Example 1 except that ester derivatives of corresponding carboxylic acids are used in place of (E,E,E)-2-(6,6-dimethyl-2-hepten-4-ynyl)-8-[3-(3-thienyl)phenyl]-2,7-octadienic acid methyl ester which is the raw material compound used in the above reaction.

EXAMPLE 2

(E,E)-2-(6,6-dimethyl-2-hepten-4-ynyl)-7-[3-(3-thienyl)phenoxy]-2-hepten-1-ol

NMR (CDCl$_3$) δ: 1.22 (9H, s), 1.50–1.63 (2H, m), 1.76–1.87 (2H, m), 2.09–2.18 (2H, m), 2.89 (2H, br.d, J=6.6Hz), 4.00 (2H, s), 4.00 (2H, t, J=6.3Hz), 5.50 (1H, dt, J=15.9Hz, 1.8Hz), 5.53 (1H, br.t, J=6.9Hz), 5.99 (1H, dt, J=15.9Hz, 6.6Hz), 6.82 (1H, br.d, J=7.5Hz), 7.12 (1H, m), 7.18 (1H, br.d, J=7.5 Hz), 7.30 (1H, t, J=7.5 Hz), 7.37

EXAMPLE 3

(E,E)-2-(6,6-dimethyl-2-hepten-4-ynyl)-4-[2-[3-(3-thienyl)phenoxy]ethoxy]-2-buten-1-ol NMR (CDCl$_3$) δ:1.22 (9H, s), 2.92 (2H, br.d, J=6.7Hz), 3.81–3.84 (2H, m), 4.06 (2H, br.s), 4.15–4.20 (4H, m), 5.50 (1H, dt, J=15.9Hz, 1.5Hz), 5.77 (1H, br.t, J=6.6Hz), 5.96 (1H, dt, J=15.9Hz, 6.7Hz), 6.85 (1H, br.d, J =8.1Hz), 7.16–7.21 (2H, m), 7.30 (1H, t, J=8.1Hz), 7.37 (1H, s), 7.38 (1H, s), 7.44 (1H, t, J=2.1Hz)

EXAMPLE 4

(E,E)-2-(6,6-dimethyl-2-hepten-4-ynyl)-3-[3-[3-(3-thienyl)phenoxymethyl]phenyl]-2-propen-1-ol NMR (CDCl$_3$) δ:1.22 (9H, s), 1.45 (1H, br.t, J=4.8Hz), 3.15 (2H, dd, J=6.6Hz, 1.2Hz), 4.19 (2H, d, J=4.8Hz), 5.10 (2H, s), 5.56 (1H, dt, J=15.9Hz, 1.2Hz), 6.06 (1H, dt, J=15.9Hz, 6.6Hz), 6.65 (1H, br.s), 6.90 (1H, ddd, J=6.7Hz, 2.4Hz, 0.5Hz), 7.18–7.39 (9H, m),7.42 (1H, dd, J=2.4Hz, 1.8Hz)

EXAMPLE 5

(E,E)-2-(6,6-dimethyl-2-hepten-4-ynyl)-3-[3-[4-(3-thienyl)-2-thienylmethoxy]phenyl]-2-propen-1-ol mp: 79°–81° C.

NMR-(CDCl$_3$) δ: 1.24 (9H, s), 1.48 (1H, t, J=6.0Hz), 3.06 (2H, dd, J=6.6Hz, 1.8Hz), 4.20 (2H, dd, J=6.0Hz, 1.2Hz), 5.22 (2H, s), 5.57 (1H, dt, J=15.9Hz, 1.8Hz), 6.09 (1H, dt, J=15.9Hz, 6.6Hz), 6.63 (1H, br.s), 6.86–6.93 (3H, m), 7.23–7.38 (6H, m)

EXAMPLE 6

(E,E,E)-2-(6,6-dimethyl-2-hepten-4-ynyl)-3-[3-[2-[3-(3-thienyl)phenyl]ethenyl]phenyl]-2-propen-1-ol mp: 99°–101° C.

NMR (CDCl$_3$) δ:1.24 (9H, s), 3.10 (2H, dd, J=6.3Hz, 1.5Hz), 4.24 (2H, br.s), 5.61 (1H, dt, J=15.9Hz, 1.5Hz), 6.14 (1H, dt, J=15.9Hz, 6.3Hz), 6.69 (1H, s), 7.12–7.52 (12H, m), 7.74 (1H, t, J=1.8Hz)

EXAMPLE 7

(E,E,E)-2-(6,6-dimethyl-2-hepten-4-ynyl)-3-[5-[3-(3-thienyl)-2-propenyloxymethyl]-2-furyl]-2-propen-1-ol NMR (CDCl$_3$) δ:1.21 (9H, s), 3.24 (2H, dd, J=6.9Hz, 1.5 Hz), 4.16 (2H, s), 4.17 (2H, dd, J=6.3Hz, 1.5Hz), 4.49 (2H, s), 5.59 (1H, dt, J=15.9Hz, 1.5Hz), 6.09 (1H, dt, J=15.9Hz, 6.9Hz), 6.14 (1H, dt, J=15.9Hz, 6.3Hz), 6.25 (1H, d, J=3.3Hz), 6.34 (1H, d, J=3.3Hz), 6.37 (1H, s), 6.63 (1H, d, J=15.9Hz), 7.15–7.30 (3H, m)

EXAMPLE 8

(E,E,E)-2-(6-methoxy-6-methyl-2-hepten-4-ynyl)-3-[3-[2-[3-(3-thienyl)phenyl]ethenyl]phenyl]-2-propen-1-ol NMR (CDCl$_3$) δ:1.46 (6H, s), 3.14 (2H, dd, J=6.3Hz, 1.2Hz), 3.35 (3H, s), 4.25 (2H, d, J=5.4Hz), 5.65 (1H, dt, J=15.9Hz, 1.5Hz), 6.24 (1H, dt, J=15.9Hz, 6.3Hz), 6.71 (1H, s), 7.14–7.53 (12H, m), 7.73 (1H, s)

EXAMPLE 9

(E,E)-2-(6,6-dimethyl-2-hepten-4-ynyl)-3-[3-[2-[3-(3-thienyl)phenyl]ethyl]phenyl]-2-propen-1-ol NMR (CDCl$_3$) δ: 1.26 (9H, s), 1.47 (1H, t, J=5.7Hz), 2.97 (4H, s), 3.03 (2H, d, J=6.3Hz), 4.21 (2H, d, J=5.7Hz), 5.57 (1H, d, J=15.9Hz), 6.08 (1H, dt, J=15.9Hz, 6.3Hz), 6.64 (1H, s), 7.07–7.14 (4H, m), 7.25–7.47 (7H, m)

EXAMPLE 10

(E,E)-2-(6-methoxy-6-methyl-2,4-heptadiynyl)-3-[3-[2-[3-(3-thienyl)phenyl]ethenyl]phenyl]-2-propen-1-ol NMR (CDCl$_3$) δ:1.45 (6H, s), 3.31 (2H, s), 3.34 (3H, s), 4.38 (2H, d, J=3.9Hz), 6.69 (1H, s), 7.15–7.53 (12H, m), 7.74 (1H, t, J=1.6Hz)

EXAMPLE 11

Preparation of (E)-2-(6,6-dimethyl-2-hepten-4-ynyl)-3-[3-[3-(3-thienyl)phenylmethoxy]phenyl]propanol 720 mg of (E)-2-(6,6-dimethyl-2-hepten-4-ynyl)-3-[3-[3-(3-thienyl)phenylmethoxy]phenyl]propionic acid methyl ester is dissolved in 30 ml of ethyl ether, 116 mg of lithium aluminum hydride is added thereto under ice cooling and stirring, and the mixture is stirred at that temperature for 1 hour. Saturated saline is added to the reaction solution to decompose the excessive reducing agent, and then extraction is carried out with addition of 40 ml of 1N hydrochloric acid and 40 ml of ethyl ether. The organic layer is taken, washed with saturated saline and dried over anhydrous magnesium sulfate, and the solvent is distilled off under reduced pressure. The residue is purified by silica gel column chromatography [Wako gel C-200, 20 g; hexane/ethyl acetate=9/1→4/1] to obtain 662 mg (yield: 98%) of the captioned compound as a colorless oily matter.

NMR (CDCl$_3$) δ:1.23 (9H, s), 1.89 (1H, m), 2.10–2.19 (2H, m), 2.61 (2H, d. J=7.8 Hz), 3.46–3.51 (2H, m), 5.09 (2H, s), 5.51 (1H, dt, J=15.9Hz, 1.5Hz), 6.01 (1H, dt, J=15.9Hz, 7.5Hz), 6.77–6.86 (3H, m), 7.18–7.50 (6H, m), 7.56 (1H, dt, J=7.5 Hz, 1.5Hz), 7.66 (1H, s)

The alcohol compounds of Examples 12 to 15 are obtained by carrying out the same reaction as in Example 11 except that methyl ester derivatives of corresponding carboxylic acids are used in place of (E)-2-(6,6-dimethyl-2-hepten-4-ynyl)-3-[3-[3-(3-thienyl)phenylmethoxy]phenyl]propionic acid methyl ester which is the raw material compound used in the above reaction.

EXAMPLE 12

(E,E)-2-(6,6-dimethyl-2-hepten-4-ynyl)-3-[3-[2-[3-(3-thienyl)phenyl]ethenyl]phenyl]propanol NMR (CDCl$_3$) δ:1.24 (9H, s), 1.86–2.06 (1H, m), 2.19 (2H, t, J=7.1Hz), 2.67 (2H, d, J=7.3Hz), 3.56 (2H, d, J=5.3Hz), 5.54 (1H, dt, J=15.7Hz, 1.4Hz), 6.06 (1H, dt, J=15.7Hz, 7.1Hz), 7.09 (1H, dt, J=7.4Hz, 1.7Hz), 7.15 (2H, s), 7.28–7.53 (9H, m), 7.73 (1H, t, J=1.2 Hz)

EXAMPLE 13

(E)-2-(6,6-dimethyl-2-hepten-4-ynyl)-7-[3-(3-thienyl)phenoxy]heptanol

NMR (CDCl$_3$) δ:1.24 (9H, s), 1.10–2.00 (10H, m), 2.15 (2H, t, J=6.8Hz), 3.55 (2H, t, J=5.0Hz), 4.00 (2H, t, J=6.5Hz), 5.45 (1H, d, J=15.9Hz), 5.99 (1H, dt, J=15.9Hz, 7.2Hz), 6.70–7.45 (7H, m)

EXAMPLE 14

(E,E,E)-2-(6,6-dimethyl-2-hepten-4-ynyl)-8-[3-(3-thienyl)phenyl]-2,7-octadien-1-ol NMR (CDCl$_3$) δ:1.21 (9H, s), 1.30–1.50 (5H, m), 2.11–2.18 (2H, m), 2.19–2.26 (2H, m), 3.51–3.58 (2H, m), 5.49 (1H, dt, J=15.9Hz, 1.5Hz), 6.00 (1H, dt, 15.9Hz, 7.8Hz), 6.24 (1H, dt, J=15.9Hz, 6.9Hz), 6.40 (1H, d, J=15.9Hz), 7.29 (1H, dt, J=7.5 Hz, 1.4Hz), 7.34 (1H, t, J=7.5Hz), 7.40 (1H, d, J=3.0Hz), 7.41 (1H, d, J=1.5 Hz), 7.44 (1H, dd, J=7.5 Hz, 1.4Hz), 7.47 (1H, dd, J=3.0Hz, 1.5Hz), 7.57 (1H, m)

EXAMPLE 15

(E)-2-(6,6-dimethyl-2-hepten-4-ynyl)-3-[3-[4-(3-thienyl)-2-thienylmethoxy]phenyl]propanol NMR (CDCl$_3$) δ:1.22 (9H, s), 1.85–2.00 (1H, m), 2.13–2.20 (2H, m), 2.64 (2H, d, J=8.1Hz), 3.46–3.52 (2H, m), 5.20 (2H, s), 5.53 (1H, dt, J=15.3Hz, 1.2Hz), 6.04 (1H, dt, J=15.3Hz, 6.4Hz), 6.81–6.88 (3H, m), 7.20–7.38 (6H, m)

EXAMPLE 16

Preparation of (E)-2-(6,6-dimethyl-2,4-heptadiynyl)-3-[3-[2-[3-(3-thienyl)phenyl]ethenyl]phenyl]propanol 980 mg of (E)-2-(6,6-dimethyl-2,4-heptadiynyl)-3-[3-[2-[3-(3-thienyl)phenyl]ethenyl]phenyl]propionic acid is dissolved in 20 ml of ethyl ether, 132 mg of lithium aluminum hydride is added in several portions thereto under ice cooling and stirring, and the mixture is stirred at that temperature for 10 minutes. Saturated saline is added to the reaction solution to decompose the excessive reducing agent, and 20 ml of 10% aqueous citric acid solution and 30 ml of ethyl ether are added to form two liquid phases. The organic layer is taken, washed successively with 5% aqueous sodium bicarbonate solution and saturated saline, and dried over anhydrous sodium sulfate. The desiccating agent is filtered, the solvent is distilled off under reduced pressure, and the residue is crudely purified by silica gel short column chromatography [hexane/ethyl acetate=1/1] and then purified by medium pressure liquid chromatography [column: Lobar column, size B, Lichroprep Si 60 F (produced by Merck Co.); eluent: hexane/ethyl acetate=5/1→3/1] to obtain 625 mg (yield: 68%) of the captioned compound as a colorless oily matter.

NMR (CDCl$_3$) δ:1.25 (9H, s), 2.00–2.15 (1H, m), 2.35–2.43 (2H, m), 2.70–2.80 (2H, m), 3.50–3.75 (2H, m), 7.10–7.55 (12H, m), 7.75 (1H, br.s)

EXAMPLE 17

(E,E)-3-(6,6-dimethyl-2-hepten-4-ynyl)-8-[3-(3-thienyl)-phenoxy]-3-octen-1-ol 117 mg of (E,E)-2-(6,6-dimethyl-2-hepten-4-ynyl)-7-[3-(3-thienyl)phenoxy]-2-hepten-1-ol obtained in Example 2 is dissolved in 5 ml of ethyl acetate, 27 μl of methanesulfonyl chloride and 60 μl of triethylamine are added, and the mixture is stirred under ice cooling for 1 hour. Saturated aqueous sodium bicarbonate solution and ethyl acetate are added to the reaction solution, the mixture is stirred at room temperature for 15 minutes, and the organic layer is taken and dried over anhydrous magnesium sulfate. The desiccating agent is filtered, the solvent is distilled off, the residue is dissolved in 5 ml of dimethylformamide, 30 mg of sodium cyanide is added, and the mixture is stirred at room temperature for 4 hours. Saturated saline and ethyl ether are added to the reaction solution to form two liquid phases, the organic layer is taken, washed with saturated saline and dried over anhydrous magnesium sulfate, and the solvent is distilled off under reduced pressure. The residue is purified by silica gel column chromatography [Wako gel C-200, 20 g; hexane/ethyl acetate=10/1] to obtain 76 mg (yield: 64%) of (E,E)-2-(6,6-dimethyl-2-hepten-4-ynyl)-8-[3-(3-thienyl)phenoxy]-3-octenenitrile as colorless oil.

72 mg of the thus obtained nitrile compound is dissolved in 3 ml of methylene chloride, 0.20 ml of 1M toluene solution of diisobutylaluminum hydride is added, and the mixture is stirred at −78° C. for 2 hours. Saturated aqueous sodium chloride solution and methylene chloride are added to the reaction solution to form two liquid phases, the organic layer is taken and dried over anhydrous magnesium sulfate, and the solvent is distilled off. The residue is dissolved in 3 ml of methanol, 13 mg of sodium borohydride is added, and the mixture is stirred under ice cooling for 1 hour. The reaction solution is concentrated under reduced pressure, the residue is extracted with a system of saturated saline and methylene chloride, the organic layer is taken and dried over anhydrous magnesium sulfate, and the solvent is distilled off under reduced pressure. The residue is purified by preparative thin layer chromatography [Kieselgel 60 F$_{254}$, Art. 5717 (produced by Merck Co.); hexane/ethyl acetate=3/1] to obtain 13 mg (yield: 18%) of the captioned compound as a colorless oily matter.

NMR (CDCl$_3$) δ:1.23 (9H, s), 1.50–1.65 (2H, m), 1.75–1.87 (2H, m), 2.07–2.17 (2H, m), 2.25 (2H, br.t, J=6.0Hz), 2.82 (2H, br.d, J=6.6Hz), 3.65 (2H, br.t, J=6.0Hz), 4.00 (2H, t, J=8.1Hz), 5.36 (1H, br.t, J=6.6Hz), 5.50 (1H, dt, J=15.9Hz, 1.8Hz), 5.94 (1H, dt, J=15.9Hz, 6.6Hz), 6.83 (1H, br.d, J=8.1Hz), 7.12 (1H, br.t, J=2.1Hz), 7.18 (1H, br.d, J=8.1Hz), 7.30 (1H, t, J=8.1Hz), 7.37 (1H, s), 7.38 (1H, s), 7.45 (1H, t, J=2.1Hz)

EXAMPLE 18

Preparation of 3-[3-[(1E,6Z,9E)-7,13,13-trimethyltetradeca-1,6,9-trien-11-ynyl]phenyl]thiophene 20 mg of (E,E,E)-2-(6,6-dimethyl-2-hepten-4-ynyl)-8-[3-(3-thienyl)phenyl]-2,7-octadien-1-ol obtained in Example 1 is dissolved in 2 ml of ethyl acetate, 4.6 μl of methanesulfonyl chloride and 10.5 μl of triethylamine are added, and the mixture is stirred under ice cooling for 1 hour. Saturated aqueous sodium bicarbonate solution and ethyl acetate are added to the reaction solution, the mixture is stirred at room temperature for 15 minutes, and the organic layer is taken and dried over anhydrous magnesium sulfate. The desiccating agent is filtered, the solvent is distilled off under reduced pressure, the residue is dissolved in 5 ml of tetrahydrofuran, 0.25 ml of 1M tetrahydrofuran solution of lithium triethylborohydride is added, and the mixture is stirred under ice cooling for 2 hours. The reaction solution is poured in saturated aqueous ammonium chloride solution, ethyl acetate is added for extraction, the extract is washed with saturated saline and dried over anhydrous magnesium sulfate, and the solvent is distilled off under reduced pressure. The residue is purified by silica gel column chromatography [Wako gel C-200, 4 g; hexane/ethyl acetate=100/1→50/1] to obtain 14 mg (yield: 72%) of the captioned compound as a colorless oily matter.

NMR (CDCl$_3$) δ:1.23 (9H, s), 1.45–1.51 (2H, m), 1.68 (3H, s), 2.06 (2H, q, J=7.0Hz), 2.23 (2H, q, J=6.6Hz), 2.78 (2H, d, J=6.6Hz), 5.25 (1H, br.t, J=7.0Hz), 5.48 (1H, dt, J=15.8Hz, 1.6Hz), 5.97 (1H, dt, J=15.8Hz, 6.6Hz), 6.26 (1H, dt, J=15.8Hz, 6.6Hz), 6.43 (1H, d, J=15.8Hz), 7.25–7.47 (6H, m), 7.55 (1H, br.s)

The compounds of Examples 19 to 27 are obtained by carrying out the same reactions as in Example 18 except that corresponding alcohol derivatives are used in place of (E,E,E)-2-(6,6-dimethyl-2-hepten-4-ynyl)-8-[3-(3-thienyl)phenyl]-2,7-octadien-1-ol which is a raw material compound used in the above reaction.

EXAMPLE 19

3-[3-[(5Z,8E)-6-ethyl-12,12-dimethyltrideca-5,8-dien-10-ynyloxy]phenyl]thiophene NMR (CDCl$_3$) δ:1.00 (3H, t, J=7.5Hz), 1.23 (9H, s), 1.48–1.60 (2H, m), 1.76–1.85 (2H, m), 1.98 (2H, br.q, J=7.5Hz), 2.08 (2H, m), 2.80 (2H, br.d, J=6.6Hz), 4.00 (2H, t, J=6.6Hz), 5.23 (1H, br.t, J=7.2Hz), 5.47 (1H, dt, J=15.6Hz, 1.5Hz), 5.96 (1H, dt, J=15.6Hz, 6.6Hz), 6.83 (1H, br.d, J=7.8Hz), 7.12 (1H, m), 7.17 (1H, br.d, J=7.8Hz), 7.30 (1H, t, J=7.8Hz), 7.37 (1H, s), 7.38 (1H, s), 7.44 (1H, t, J=2.3Hz)

EXAMPLE 20

3-[3-[2-[(2Z,5E)-3,9,9-trimethyldeca-2,5-dien-7-ynyloxy]ethoxy]phenyl]thiophene

NMR (CDCl$_3$) δ:1.23 (9H, s), 1.74 (3H, br.s), 2.85 (2H, br.d, J=6.6Hz), 3.79 (2H, t, J=4.8Hz), 4.08 (2H, br.d, J=6.6Hz), 4.17 (2H, t, J=4.8Hz), 5.46–5.51 (2H, m), 5.96 (1H, dt, J=15.9Hz, 6.6Hz), 6.85 (1H, br.d, J=8.1Hz), 7.16–7.20 (2H, m), 7.30 (1H, t, J=8.1Hz), 7.37 (1H, s), 7.38 (1H, s), 7.44 (1H, t, J=2.1Hz)

EXAMPLE 21

3-[3-[3-[(1Z,4E)-2,8,8-trimethylnona-1,4-dien-6-ynyl]phenylmethoxy]phenyl]thiophene NMR (CDCl$_3$) δ: 1.25 (9H, s), 1.88 (3H, d, J=1.5Hz), 2.96 (2H, dd, J=6.6Hz, 1.5Hz), 5.11 (2H, s), 5.56 (1H, dt, J=15.9Hz, 1.6Hz), 6.10 (1H, dt, J=15.9Hz, 6.6Hz), 6.40 (1H, br.s), 6.94 (1H, ddd, J=6.7Hz, 2.3Hz, 0.5Hz), 7.15–7.40 (9H, m), 7.45 (1H, dd, J=2.3Hz, 2.1Hz)

EXAMPLE 22

2-[3-[(1Z,4E)-2,8,8-trimethylnona-1,4-dien-6-ynyl]-phenoxymethyl]-4-(3-thienyl)thiophene NMR (CDCl$_3$) δ:1.26 (9H, s), 1.88 (3H, d, J=1.5Hz), 2.98 (2H, dd, J=6.3Hz, 1.3Hz), 5.23 (2H, s), 5.56 (1H, dt, J=15.9Hz, 1.3Hz), 6.10 (1H, dt, J=15.9Hz, 6.3Hz), 6.37 (1H, br.s), 6.83–6.88 (3H, m), 7.22–7.39 (6H, m)

EXAMPLE 23

3-[3-[2-[3-[(1Z,4E)-2,8,8-trimethylnona-1,4-dien-6-ynyl]phenyl]ethenyl]phenyl]thiophene NMR (CDCl$_3$) δ: 1.25 (9H, s), 1.90 (3H, br.s), 3.00 (1H, d, J=6.3Hz), 5.60 (1H, br.d, J=15.9Hz), 6.13 (1H, dt, J=15.9Hz, 6.3Hz), 6.41 (1H, s), 7.07–7.51 (2H, m), 7.73 (1H, s)

EXAMPLE 24

Preparation of (E)-3-[3-[3-(2,8,8-trimethyl-4-nonen-6-ynyl)phenoxymethy]phenyl]thiophene NMR (CDCl$_3$) δ:0.86 (3H, d, J=6.6Hz), 1.24 (9H, s), 1.77–1.86 (1H, m), 1.88–1.99 (1H, m), 2.06–2.17 (1H, m), 2.36 (1H, dd, J=13.5Hz, 8.6Hz); 2.61 (1H, dd, J=13.5Hz, 6.0Hz), 5.09 (2H, s), 5.46 (1H, dt, J=15.6Hz, 1.5Hz), 6.02 (1H, dt, J=15.6Hz, 7.5Hz), 7.74–7.86 (3H, m), 7.19 (1H, t, J=7.5Hz), 7.34–7.50 (5H, m), 7.55 (1H, dt, J=7.8Hz, 1.5Hz), 7.67 (1 H, s)

EXAMPLE 25

(E,E)-3-[3-[2-[3-(2,8,8-trimethyl-4-nonen-6-ynyl)-phenyl]ethenyl]phenyl]thiophene NMR (CDCl$_3$) δ:0.90 (3H, d, J=6.4Hz), 1.24 (9H, s), 1.85–2.16 (3H, m), 2.40 (1H, dd, J=13.3Hz, 7.7Hz), 2.68 (1H, dd, J=13.3Hz, 6.0Hz), 5.49 (1H, d, J=15.8Hz). 6.06 (1H, dt, J=15.8Hz, 7.4Hz), 7.05 (1H, d, J=7.3Hz), 7.14 (2H, s), 7.18–7.55 (9H, m), 7.73 (1H, s)

EXAMPLE 26

(E)-3-[3-(6,12,12-trimethyl-8-tridecen-10-ynyloxy)]-phenyl]thiophene

NMR (CDCl$_3$) δ:0.87 (3H, d, J=6.6Hz), 1.24 (9H, s), 1.11–1.59 (7H, m), 1.80 (2H, q, J=6.6Hz), 1.92 (1H, m), 2.07 (1H, m), 4.00 (2H, t, J=6.6Hz), 5.45 (1H, d, J=15.9Hz), 5.99 (1H, dt, J=15.9Hz, 7.2Hz), 6.83 (1H, dd, J=7.8Hz, 2.4Hz), 7.10–7.20 (2H, m), 7.30 (1H, t, J=7.8Hz), 7.37 (2H, d, J=2.1Hz), 7.44 (1H, t, J=2.1Hz)

EXAMPLE 27

(E)-3-[3-[2-[3-[(1Z,4E)-8-methoxy-2,8-dimethylnona-1,4-dien-6-ynyl]phenyl]ethenyl]phenyl]thiophene mp: 57°–59° C.

NMR (CDCl$_3$) δ: 1.47 (6H, s), 1.91 (3H, d, J=1.5Hz), 3.03 (2H, dd, J=1.5Hz, 6.6Hz), 3.36 (3H, s), 5.62 (1H, dt, J=15.9Hz, 1.5Hz), 6.23 (1H, dt, J=15.9Hz, 6.6Hz), 6.44 (1H, s), 7.07–7.52 (12H, m), 7.73 (1H, t, J=1.8Hz)

EXAMPLE 28

3-[3-[(5Z,8E)-6,12,12-trimethyltrideca-5,8-dien-10-ynyloxy]phenyl]thiophene 750 mg of (E)-2-(6,6-dimethyl-2-hepten-4-ynyl)-7-[3-(3-thienyl)phenoxy]-3-oxoheptanoic acid methyl ester is dissolved in 10 ml of tetrahydrofuran, 0.16 ml of methyl iodide and 85 mg of 60% oily sodium hydride are added under ice cooling and stirring, and the mixture is stirred for 3 hours under ice cooling. The reaction solution is diluted with water, acetic acid is added for neutralization to pH 7, extraction is made with ethyl acetate, the extract is washed with saturated saline and dried over anhydrous magnesium sulfate, and then the solvent is distilled off under reduced pressure. The residue is purified by silica gel column chromatography [Wako gel C-200, 30 g; hexane/ethyl acetate=6/1] to obtain 705 mg (yield: 92%) of (E)-2-methyl-2-(6,6-dimethyl-2-hepten-4-ynyl)-7-[3-(3-thienyl)phenoxy]-3-oxoheptanoic acid methyl ester as colorless oil.

537 mg of the thus obtained methyl compound is dissolved in 8 ml of ethanol, 4 ml of 1N aqueous sodium hydroxide solution is added, and the mixture is held at 70° C. for 2 hours, acidified with 1N hydrochloric acid and then heated under reflux for 2 hours. The reaction solution is concentrated under reduced pressure, the residue is dissolved in a mixture of water with ethyl acetate, the organic layer is taken, washed with saturated saline and dried over anhydrous magnesium sulfate, and the solvent is distilled off under reduced pressure. The residue is purified by silica gel column chromatography [Wako gel C-200, 25 g; hexane/ethyl acetate=6/1] to obtain 416 mg (yield: 86%) of (E)-6,12,12-trimethyl-1-[3-(3-thienyl)phenoxy]tridec-8-en-10-yn-5-one as colorless oil.

339 mg of the thus obtained ketone compound is dissolved in 5 ml of ethanol, 84 ml of sodium borohydride is added, and the mixture is stirred at room temperature for 1.5 hours. The reaction solution is concentrated under reduced pressure, the residue is extracted with a system of water and methylene chloride, the organic layer is treated in a conventional manner, and then purification by silica gel column chromatography [Wako gel C-200, 25 g; hexane/ethyl acetate=4/1] is carried out to obtain 231 mg (yield: 68%) of (E)-6,12,12-trimethyl-1-[3-(3-thienyl)phenoxy]tridec-8-en-10-yn-5-ol as colorless oil.

189 mg of the thus obtained alcohol compound is dissolved in 5 ml of methylene chloride, 40 μl of methanesulfonyl chloride and 173 mg of 4-dimethylaminopyridine are added, and the mixture is stirred at room temperature for 2 days. The reaction solution is washed successively with saturated aqueous sodium bicarbonate solution and saturated saline and dried over anhydrous magnesium sulfate, and the solvent is distilled off under reduced pressure. The residue is dissolved in 5 ml of toluene, 153 mg of 1,8-diazabicyclo[5.4.0]-7-undecene is added, and the mixture is heated at 100° C. for 19 hours. The reaction solution is concentrated under reduced pressure, and purified by silica gel column chromatography [Wako gel C-300, 30 g; hexane/ethyl acetate=100/1→50/1] and then by reverse-phase high pressure liquid chromatography [column: Capcell PaK C$_{18}$ (produced by Shiseido Co., Ltd.), mobile phase: methanol/water=6/1] to obtain 4.3 mg (yield: 2.5%) of the captioned compound as a colorless oily matter.

NMR (CDCl$_3$) δ: 1.23 (9H, s), 1.48–1.61 (2H, m), 1.70–1.90 (2H, m), 2.00–2.12 (2H, m), 2.78 (2H, br.d, J=6.6Hz), 4.00 (2H, t, J=6.4 Hz), 5.25 (1H, br.t, J=6.8Hz), 5.47 (1H, br.d, J=16Hz), 5.96 (1H, dt, J=16.0Hz, 6.6Hz), 6.83 (1H, br.d, J=7.6Hz), 7.10–7.22 (2H, m), 7.30 (1H, t, J=7.6Hz), 7.37 (1H, S), 7.45 (1H, t, J=2.2Hz)

EXAMPLE 29

Preparation of
(E,E,E)-3-[3-(7-methoxymethyl-13,13-dimethyltetradeca-1,6,9-trien-11-ynyl)phenyl]thiophene 19.6 mg of (E,E,E)-2-(6,6-dimethyl-2-hepten-4-ynyl)-8-[3-(3-thienyl)phenyl]-2,7-octadien-1-ol obtained in Example 1 is dissolved in 2 ml of tetrahydrofuran, 11.2 mg of 60% oily sodium hydride and 60 μl of methyl iodide are added under ice cooling and stirring, and the mixture is stirred at room temperature for 4 hours. Water and ethyl ether are added to the reaction solution for dilution, and the organic layer is taken, washed with saturated saline and dried over anhydrous magnesium sulfate. The desiccating agent is filtered, the solvent is distilled off under reduced pressure, and the residue is purified by preparative thin layer chromatography [Kieselgel 60 $F_{254}$, Art. 5717 (produced by Merck Co.); hexane/ethyl acetate=9/1] to obtain 10.2 mg (yield: 50%) of the captioned compound as a colorless oily matter.

NMR (CDCl$_3$) δ: 1.22 (9H, s), 1.52–1.63 (2H, m), 2.11 (2H, dt, J=14.7Hz, 6.9Hz), 2.24 (2H, dt, J=13.8 Hz, 6.5 Hz), 2.85 (2H, br.d, J=6.6Hz), 3.28 (3H, s), 3.79 (2H, s), 5.48 (1H, dt, J=15.9Hz, 1.5Hz), 5.53 (1H, br.t, J=6.5 Hz), 5.97 (1H, dt, J=15.9Hz, 6.6Hz), 6.26 (1H, dt, J=15.9Hz, 6.9Hz), 6.43 (1H, d, J=15.9Hz), 7.28–7.31 (1H, m), 7.32 (1H, t, J=7.8Hz), 7.38–7.46 (4H, m), 7.55 (1H, m)

The compounds of Examples 30 and 31 are obtained by carrying out the same reaction as in Example 29 except that (E,E)-2-(6,6-dimethyl-2-hepten-4-ynyl)-7-[3-(3-thienyl)phenoxy]-2-hepten-1-ol and/or ethyl iodide are used in place of (E,E,E)-2-(6,6-dimethyl-2-hepten-4-ynyl)-8-[3-(3-thienyl)phenyl]-2,7-octadien-1-ol and/or methyl iodide which is the raw material compound used in the above reaction.

EXAMPLE 30

(E,E)-3-[3-(6-methoxymethyl-12,12-dimethyltrideca-5,8-dien-10-ynyloxy)phenyl]thiophene NMR (CDCl$_3$) δ: 1.23 (9H, s), 1.50–1.62 (2H, m), 1.78–1.87 (2H, m), 2.13 (2H, dt, J=7.2Hz, 5.7Hz), 2.85 (2H, br.d, J=6.9Hz), 3.27 (3H, s), 3.78 (2H, s), 4.00 (2H, t, J=6.3Hz), 5.48 (1H, dt, J=15.6Hz, 1.5Hz), 5.53 (1H, br.t, J=7.2Hz), 5.97 (1H, dt, J=15.6Hz, 6.9Hz), 6.38 (1H, br.d, J=7.8Hz), 7.12 (1H, m), 7.17 (1H, br.d, J=7.8Hz), 7.30 (1H, t, J=7.8Hz), 7.37 (1H, s), 7.38 (1H, s), 7.44 (1H, t, J=

EXAMPLE 31

(E,E)-3-[3-(6-ethoxymethyl-12,12-dimethyltrideca-5,8-dien-10-ynyloxy)phenyl]thiophene NMR (CDCl$_3$) δ:1.19 (3H, t, J=7.0Hz), 1.23 (9H, s), 1.50–1.70 (2H, m), 1.75–1.88 (2H, m), 2.07–2.20 (2H, m), 2.88 (2H, br.d, J=6.6Hz), 3.42 (2H, q, J=7.0Hz), 3.83 (2H, br.s), 4.01 (2H, t, J=6.4Hz), 5.48 (1H, dt, J=15.8Hz, 1.6Hz), 5.52 (1H, br.t, J=7.0Hz), m), 7.18 (1H, br.d, J=8.0Hz), 7.30 (1H, t, J=8.0Hz), 7.37 (1H, s), 7.38 (1H, s), 7.45 (1H, t, J=2.2Hz)

EXAMPLE 32

Preparation of
(E)-3-[3-[3-(2-methoxymethyl-8,8-dimethyl-4-nonen-6-ynyl)phenoxymethyl]phenyl]thiophene 44.4 mg of (E)-2-(6,6-dimethyl-2-hepten-4-ynyl)-3-[3-[3-(3-thienyl)phenylmethoxy]phenyl]propanol obtained in Example 11 is dissolved in 1 ml of dimethylformamide, 17.4 μl of methyl iodide and 8 mg of 60% oily sodium hydride are added under ice cooling and stirring, and the mixture is stirred at room temperature for 4 hours. Water and ethyl ether are added to the reaction solution for dilution, and the organic layer is taken, washed with saturated saline and dried over anhydrous magnesium sulfate. The desiccating agent is filtered, the solvent is distilled off under reduced pressure, and the residue is purified by silica gel column chromatography [Wako gel C-200, 7 g; hexane/ethyl acetate=19/1] to obtain 39 mg (yield: 80%) of the captioned compound as a colorless oily matter.

NMR (CDCl$_3$) δ:1.24 (9H, s), 1.96 (1H, m), 2.05–2.20 (2H, m), 2.50–2.70 (2H, m), 3.20 (2H, d, J=5.4Hz), 3.29 (3H, s), 5.09 (2H, s), 5.48 (1H, dt, J=16.2Hz, 1.5Hz), 5.99 (1H, dt, J=16.2Hz, 7.2Hz), 6.75–6.86 (3H, m), 7.20 (1H, t, J=7.8Hz), 7.34–7.49 (5H, m), 7.55 (1H, dt, J=7.5Hz, 1.8Hz), 7.67 (1H, br.s)

EXAMPLE 33

Preparation of
(E,E)-2-[3-(2-methoxymethyl-8,8-dimethylnona-1,4-dien-6-ynyl)phenoxymethyl]-4-(3-thienyl)thiophene 1.03 g of (E,E)-2-(6,6-dimethyl-2-hepten-4-ynyl)-3-[3-[4-(3-thienyl)-2-thienylmethoxy]phenyl]-2-propen-1-ol obtained in Example 5 and 3 ml of methyl iodide are dissolved in a solution consisting of 18 ml of tetrahydrofuran and 2 ml of dimethylformamide, 0.11 g of 60% oily sodium hydride is added in several portions under ice cooling and stirring, and the mixture is stirred under ice cooling for 2 hours and then at room temperature for 5 hours. Acetic acid is added to the reaction solution to make it weakly acidic, the solvent is distilled off under reduced pressure, the residue is dissolved in a mixture of water with ethyl acetate, and the organic layer is taken. The extract is washed with saturated saline and dried over anhydrous magnesium sulfate, the desiccating agent is filtered, and the solvent is distilled off under reduced pressure. The residue is treated by silica gel short column chromatography [Wako gel C-200, 10 g; hexane/ethyl acetate=10/1] and medium pressure liquid chromatography [column: Lobar column: size B, Lichroprep Si 60F (produced by Merck Co.); eluent: hexane/ethyl acetate=50/1→15/1] to obtain 0.51 g (yield: 48%) of the captioned compound as a white crystalline solid of m.p. of 67°–68° C.

NMR (CDCl$_3$) δ:1.23 (9H, s), 3.03 (2H, dd, J=6.3Hz, 1.2Hz), 3.37 (3H, s), 3.95 (2H, d, J=1.2Hz), 5.21 (2H, s), 5.55 (1H, dt, J=15.9Hz, 1.2Hz), 6.79 (1H, dt, J=15.9Hz, 6.3Hz), 6.60 (1H, t, J=1.2Hz), 6.86–6.90 (3H, m), 7.22–7.37 (6H, m)

The compounds of Examples 34 to 40 are obtained by carrying out the same reaction as in Example 33 except that corresponding alcohol derivatives are used in place of (E,E)-2-(6,6-dimethyl-2-hepten-4-ynyl)-3-[3-[4-(3-thienyl)-2-thienylmethoxy]phenyl]-2-propen-1-ol which is the raw material compound used in the above reaction.

EXAMPLE 34

(E,E)-3-[3-[2-[3-(2-methoxymethyl-8,8-dimethyl-4-nonen-6-ynyl)phenyl]ethenyl]phenyl]thiophene NMR (CDCl$_3$) δ:1.25 (9H, s), 2.00 (1H, m), 2.08–2.25 (2H, m), 2.61 (1H, dd, J=13.5Hz, 6.6Hz), 2.69 (1H, dd, J=13.5Hz, 7.2Hz), 3.24 (2H, d, J=5.4Hz), 3.36 (3H, s), 5.51 (1H, dt, J=15.9Hz, 1.5Hz), 6.03 (1H, dt, J=15.9Hz, 7.5Hz), 7.05–7.52 (10H, m), 7.73 (1H, t, J=1.8Hz)

EXAMPLE 35

(E,E)-3-[3-(7-methoxymethyl-13,13-dimethyltetradeca-1,9-dien-11-ynyl)phenyl]thiophene NMR (CDCl$_3$) δ:1.25 (9H, s), 1.31–1.43 (2H, m), 1.43–1.54 (2H, m), 1.68 (1H, m), 2.05 (2H, m), 3.26 (2H, J=5.9Hz), 3.33 (3H, s), 5.49 (1H, dt, J=15.9Hz, 1.5Hz), 6.01 (1H, dt, J=15.9Hz, 7.6Hz), 6.28 (1H, dt, J=15.9Hz, 6.9Hz), 6.43 (1H, d, J=15.9Hz), 7.29 (1H, dt, J=7.5Hz, 1.4Hz), 7.34 (1H, t, J=7.5Hz), 7.40 (1H, d, J=3.0Hz), 7.41 (1H, d, J=1.5Hz), 7.44 (1H, dt, J=7.5Hz, 1.4Hz), 7.47 (1H, dd, J=3.0Hz, 1.5Hz), 7.57 (1H, m)

EXAMPLE 36

(E)-3-[3-[2-[3-(2-methoxymethyl-8,8-dimethyl-4,6-nonadiynyl)phenyl]ethenyl]phenyl]thiophene NMR (CDCl$_3$) δ:1.26 (9H, s), 2.06–2.18 (1H, m), 2.33 (1H, dd, J=17.1Hz, 5.5Hz), 2.36 (1H, dd, J=17.1Hz, 6.1Hz), 2.71 (1H, dd, J=13.2Hz, 7.5Hz), 2.76 (1H, dd, J=13.2Hz, 7.1Hz), 3.35 (3H, s), 3.35 (2H, d, J=5.5Hz), 7.10 (1H, dt, J=7.6Hz, 1.5Hz), 7.15 (2H, s), 7.29 (1H, t, J=7.7Hz), 7.35–7.52 (8H, m), 7.73 (1H, t, J=1.6Hz)

EXAMPLE 37

(E,E,E)-3-[3-[2-[3-(2-methoxymethyl-8,8-dimethyl-nona-1,4-dien-6-ynyl)phenyl]ethenyl]phenyl]thiophene mp: 98°–99° C.

NMR (CDCl$_3$) δ:1.23 (9H, s), 3.06 (2H, dd, J=6.5Hz, 1.5Hz), 3.39 (3H, s), 3.99 (2H, d, J=0.9Hz), 5.60 (1H, dt, J=15.9Hz, 1.7Hz), 6.13 (1H, dt, J=15.9Hz, 6.5Hz), 6.65 (1H, s), 7.15 (3H, s), 7.30–7.50 (9H, m), 7.73 (1H, m)

EXAMPLE 38

(E,E)-3-[3-[2-[3-(2-methoxymethyl-8,8-dimethylnona-1,4-dien-6-ynyl)phenyl]ethyl]phenyl]thiophene NMR (CDCl$_3$) δ:1.24 (9H, s), 2.96 (4H, s), 2.99 (2H, dd, J=6.0Hz, 1.0Hz), 3.36 (3H, s), 3.95 (2H, s), 5.54 (1H, dt, J=15.9Hz, 1.0Hz), 6.06 (1H, dt, J=15.9Hz, 6.0Hz), 6.59 (1H, s), 7.08–7.13 (4H, m), 7.23–7.44 (7H, m)

EXAMPLE 39

(E)-2-[3-(2-methoxymethyl-8,8-dimethyl-4-nonen-6-ynyl)phenoxymethyl]-4-(3-thienyl)thiophene NMR (CDCl$_3$) δ:1.26 (9H, s), 1.90–2.01 (1H, m), 2.06–2.22 (2H, m), 2.54–2.70 (2H, m), 3.22 (2H, d, J=5.7Hz), 3.31 (3H, s), 5.22 (2H, s), 5.49 (1H, dt, J=15.9Hz, 8.4Hz), 6.79–6.87 (3H, m), 7.27–7.37 (6H, m)

EXAMPLE 40

(E,E,E)-5-(2-methoxymethyl-8,8-dimethylnona-1,4-dien-6-ynyl)-2-[3-(3-thienyl)-2-propenyloxymethyl]furan NMR (CDCl$_3$) δ:1.21 (9H, s), 3.21 (2H, dd, J=6.6Hz, 1.5Hz), 3.33 (3H, s), 3.93 (2H, s), 4.16 (2H, dd, J=6.0Hz, 1.5Hz), 4.49 (2H, s), 5.57 (1H, dt, J=15.9Hz, 1.5Hz), 6.07 (1H, dt, J=15.9Hz, 6.6Hz), 6.14 (1H, dt, J=15.9Hz, 6.0Hz), 6.25 (1H, d, J=3.3Hz), 6.32–6.36 (2H, m), 6.62 (1H, d, J=15.9Hz), 7.15–7.28 (3H, m)

EXAMPLE 41

Preparation of (E,E)-2-(6,6-dimethyl-2-hepten-4-ynyl)-7-[3-(3-thienyl)-phenoxy]-2-heptenyl acetate 18.8 mg of (E,E)-2-(6,6-dimethyl-2-hepten-4-ynyl)-7-[3-(3-thienyl)phenoxy]-2-hepten-1-ol obtained in Example 2 is dissolved in 2 ml of pyridine, 1 ml of acetic anhydride is added, and the mixture is stirred at room temperature for 18 hours. The reaction solution is concentrated under reduced pressure, water and ethyl acetate are added to the residue for extraction, the organic layer is taken, washed successively with 1N hydrochloric acid, saturated aqueous sodium bicarbonate solution and saturated saline and dried over anhydrous magnesium sulfate, and the solvent is distilled off under reduced pressure. The residue is purified by preparative thin layer chromatography [Kieselgel 60 F$_{254}$, Art. 5717 (produced by Merck Co.); hexane/ethyl acetate=5/1] to obtain 18.8 mg (yield: 91%) of the captioned compound as a colorless oily matter.

NMR (CDCl$_3$) δ:1.22 (9H, s), 1.50–1.65 (2H, m), 1.73–1.90 (2H, m), 2.06 (3H, s), 2.05–2.21 (2H, m), 2.88 (2H, br.d, J=6.6Hz), 4.04 (2H, t, J=6.4Hz), 4.46 (2H, br.s), 5.48 (1H, dt, J=16.0Hz, 1.0Hz), 5.60 (1H, br.t, J=7.2Hz), 5.96 (1H, dt, J=16.0Hz, 6.6Hz), 6.82 (1H, br.d, J=8.0Hz), 7.12 (1H, m), 7.18 (1H, m), 7.30 (1H, t, J=8.0Hz), 7.37 (1H, s), 7.39 (1H, s), 7.45 (1H, t, J=2.2Hz)

EXAMPLE 42

Preparation of (E,E)-3-[3-(12,12-dimethyl-6-methylthiomethyltrideca-5,8-dien-10-ynyloxy)phenyl]thiophene 66 mg of (E,E)-2-(6,6-dimethyl-2-hepten-4-ynyl)-7-[3-(3-thienyl)phenoxy]-2-heptenyl methanesulfonate obtained in the same manner as in Example 17 is dissolved in 5 ml of methanol, 0.2 ml of 15% aqueous solution of sodium methanethiolate is added, and the mixture is stirred at room temperature for 2 hours. The reaction solution is concentrated under reduced pressure, the residue is extracted with a system of water and ethyl ether, the organic layer is taken, washed with saturated saline and dried over anhydrous magnesium sulfate, and then the solvent is distilled off under reduced pressure. The residue is purified by preparative thin layer chromatography [Kieselgel 60 F$_{254}$, Art. 5717 (produced by Merck Co.); hexane/ethyl acetate=9/1] to obtain 37.4 mg (yield: 85%) of the captioned compound as a colorless oily matter.

NMR (CDCl$_3$) δ:1.23 (9H, s), 1.50–1.65 (2H, m), 1.73–1.88 (2H, m), 1.93 (3H, s), 2.06–2.20 (2H, m), 2.95 (2H, br.d, J=6.6Hz), 3.05 (2H, s), 4.01 (2H, t, J=6.4Hz), 5.36 (1H, br.t, J=7.4Hz), 5.50 (1H, br.d, J=15.8Hz), 5.96 (1H, dt, J=15.8Hz, 6.6Hz), 6.83 (1H, br.d, J=7.8Hz), 7.12 (1H, m), 7.17 (1H, br.d, J=7.8Hz), 7.30 (1H, t, J=7.8Hz), 7.37 (1H, s), 7.38 (1H, s), 7.45 (1H, t, J=2.1Hz)

EXAMPLE 43

Preparation of (E,E)-3-(6,6-dimethyl-2-hepten-4-ynyl)-4-[3-[2-[3-(3-thienyl)phenyl]ethenyl]phenyl]-2-butanol 44 μl of oxalyl chloride is added dropwise to a mixture of 3.6 μl of dimethyl sulfoxide with 2 μl of methylene chloride under a nitrogen atmosphere and under cooling at −78° C. and stirring, and the mixture is stirred at that temperature for 10 minutes. A methylene chloride solution (0.4 ml) of 105 mg of (E,E)-2-(6,6-dimethyl-2-hepten-4-ynyl)-3-[3-[2-[3-(3-thienyl)phenyl]ethenyl]phenyl]propanol obtained in Example 12 is added dropwise to this solution under cooling at −78° C. and stirring, the mixture is stirred at that temperature for 20 minutes, 200 μl of triethylamine is added, and the mixture is further stirred at −78° C. for 20 minutes. The solvent is distilled off under reduced pressure, the residue is led to two liquid phases using a system of water and ethyl ether, the organic layer is washed with saturated saline and dried over anhydrous magnesium sulfate, and then the solvent is distilled off under reduced pressure. The residue is purified by medium pressure liquid chromatography [column: Lobar column: size A, Lichroprep Si 60F (produced by Merck Co.); eluent: hexane/ethyl acetate=20/1] to obtain 76.6 mg (yield: 73%) of (E)-2-(6,6-dimethyl-2-hepten-4-ynyl)-3-[3-[2-[3-(3-thienyl)phenyl]ethenyl]phenyl]propionaldehyde as a colorless oily matter.

24 mg of the thus obtained aldehyde compound is dissolved in 2 ml of ethyl ether, 200 μl of 1M ethyl ether solution of methyllithium is added under a nitrogen atmosphere and under cooling at −78° C. and stirring, cooling is stopped, and the mixture is stirred for 10 minutes. Water and ethyl ether are added to the reaction solution for dilution, the organic layer is taken, washed with saturated saline and dried over anhydrous magnesium sulfate, and then the solvent is distilled off under reduced pressure. The residue is purified by medium pressure liquid chromatography [column: Lobar column, size A, Lichroprep Si 60F (produced by Merck Co.); eluent: hexane/ethyl acetate=10/1→5/1] to obtain 18 mg (yield: 73%) of the captioned compound as a colorless oily matter.

NMR (CDCl$_3$) δ: 1.18–1.26 (3H, m), 1.24 (9H, s), 1.80–1.92 (1H, m), 2.00–2.32 (2H, m), 2.53–2.64 (1H, m), 2.72–2.82 (1H, m), 3.82–3.90 (1H, m), 5.51 (1H, dt, J=15.9Hz, 1.5Hz), 5.97–6.11 (1H, m), 7.06–7.11 (11H, m), 7.15 (2H, s), 7.25–7.51 (9H, m), 7.73 (1H, t, J=1.3Hz).

EXAMPLE 44

Preparation of (E,E)-3-[2-[3-(2-ethenyl-8,8-dimethyl-4-nonen-6-ynyl)-phenyl]ethenyl]phenyl]thiophene 100 mg of methyltriphenylphosphonium bromide is dissolved in 1 ml of tetrahydrofuran, 200 μl of 1.6M hexane solution of n-butyllithium is added under cooling at −78° C. and stirring, and the mixture is stirred at room temperature for 10 minutes. The reaction solution is cooled again at −78° C., tetrahydrofuran solution (0.4 ml) of 32 mg of (E)-2-(6,6-dimethyl-2-hepten-4-ynyl)-3-[3-[2-[3-(3-thienyl)phenyl]ethenyl]phenyl]propionaldehyde obtained in Example 43 is added under stirring, and the mixture is stirred at that temperature for 20 minutes and then at room temperature for 20 minutes. The reaction solution is diluted with hexane, and the insoluble matter is filtered and the solvent is distilled off under reduced pressure. The residue is purified by silica gel column chromatography [Wako gel C-200, 5 g; hexane/ethyl acetate=20/1] to obtain 29 mg (yield: 91% of the captioned compound as a colorless oily matter.

NMR (CDCl$_3$)δ: 1.24 (9H, s), 2.19–226 (2H, m), 2.46 (1H, six, J=6.7Hz), 2.63 (1H, dd, J=13.5Hz, 7.6Hz), 2.72 (1H, dd, J=13.5Hz, 6.7Hz), 4.94 (1H, ddd, J=17.1Hz, 1.6Hz, 1.2Hz), 5.00 (1H, ddd, J=10.5Hz, 1.6Hz, 0.8Hz), 5.48 (1H, dt, J=16.2Hz, 1.5Hz), 5.69 (1 H, ddd, J=17.1Hz, 10.5Hz, 7.8Hz), 6.02 (1H, dt, J=16.2Hz, 7.2Hz), 7.05 (1H, dt, J=7.6Hz, 1.5Hz), 7.14 (2H, s), 7.24–7.51 (9H, m), 7.73 (1H, t, J=1.6Hz)

EXAMPLE 45

Preparation of powder containing the compound of Example 33 as a main chemical 25 parts of the compound of Example 33 is dissolved in a mixture consisting 500 parts each of ethanol and chloroform, 75 parts of polyvinylpyrrolidone K-30 is added, and the mixture is concentrated to dryness under reduced pressure by a conventional method. The residual solid matter is pulverized into fine particles, 250 parts of lactose, 145 parts of corn starch and 5 parts of magnesium stearate are added, and the mixture is mixed uniformly to obtain powder containing 25 mg of the main chemical in 500 mg thereof.

EXAMPLE 46

Preparation of capsules containing the compound of Example 33 as a main chemical 25 parts of the compound of Example 33 is dissolved in a mixture consisting 500 parts each of ethanol and chloroform, 72.5 parts of polyvinylpyrrolidone K-30 and 2.5 parts of Tween 60 are added, and the mixture is concentrated to dryness under reduced pressure in a conventional manner. The residual solid matter is pulverized into fine particles, 50 parts of lactose, 45 parts of corn starch and 5 parts of magnesium stearate are added, and the mixture is uniformly mixed, and 200 mg portions thereof are packed into gelatin hard capsules to obtain capsules containing 25 mg of the main chemical per capsule.

EXAMPLE 47

Preparation of capsules containing the compound of Example 33 as a main chemical 25 parts of the compound of Example 33 is suspended in 1,000 parts of water, 150 parts of β-cyclodextrin is added, the mixture is stirred at room temperature for 12 hours, 1,000 parts of water is added, and the mixture is stirred at room temperature for 3 hours. The mixture is freeze-dried by a conventional manner, the resultant cotton-like solid is softly pulverized, 70 mg portions thereof are packed into gelatin hard capsules to obtain capsules containing 10 mg of the main chemical per capsule.

REFERENTIAL EXAMPLE 1

Preparation of (E,E,E)-2-(6,6-dimethyl-2-hepten-4-ynyl)-8-[3-[3-thienyl)phenyl]-2,7-octadienic acid methyl ester 44.6 g of 4-cyanobutyltriphenylphosphonium bromide is dissolved in 250 ml of dimethylformamide, 4.2 g of 60% oily sodium hydride is added under ice cooling and stirring, then mixture is stirred at that temperature for 30 minutes, 18 g of 3-(3-thienyl)benzaldehyde is added, and the mixture is stirred at room temperature for further 20 hours. The reaction solution is diluted with water, acetic acid is added for neutralization, and then the solvent is distilled off under reduced pressure. The residue is led to two liquid phases using a system of water and ethyl ether, the organic layer is taken, washed with saturated saline and dried over anhydrous magnesium sulfate, and then the solvent is distilled off under reduced pressure. The residue is purified by silica gel column chromatography [Wako gel C-100, 500 g; hexane/ethyl acetate=4/1] to obtain 23.2 g (E)-6-[3-(3-thienyl)phenyl]-5-hexenenitrile as colorless oil.

3.64 g of the above nitrile compound and 3.92 g of activated zinc powder are added to 50 ml of tetrahydrofuran, 4.54 ml of bromoacetic acid methyl ester is added dropwise to this mixture over a period of 1 hour under reflux with heating and stirring, and the mixture is further stirred under reflux for 1 hour. 100 ml of 10% hydrochloric acid is added to the reaction solution, the mixture is stirred at room temperature for 30 minutes, tetrahydrofuran is distilled off under reduced pressure, and methylene chloride is added to the residual solution for extraction. The extract is washed with saturated saline and post-treated in a conventional manner, and the product is purified by silica gel column chromatography [Wako gel C-200, 100 g; hexane/ethyl acetate=4/1] to obtain 2.33 g of (E)-8-[3-(3-thienyl)phenyl]-3-oxo-7-octenoic acid methyl ester as colorless oil.

1.31 g of the thus obtained β-keto compound is dissolved in 20 ml of tetrahydrofuran, 174 mg of 60% oily sodium hydride and 885 mg of (E)-6,6-dimethyl-2-hepten-4-ynyl bromide (containing about 5% Z-form) are added under ice cooling and stirring, and the mixture is stirred under ice cooling for 3 hours. Acetic acid is added to the reaction solution for neutralization, water and ethyl acetate are added for extraction, the organic layer is taken and post-treated in a conventional manner, and the product is purified by silica gel column chromatography [Wako gel C-200, 60 g; hexane/ethyl acetate=10/1] to obtain 609 mg of (E,E)-2-(6,6-dimethyl-2-hepten-4-ynyl)-8-[3-(3-thienyl)phenyl]-3-oxo-7-octenoic acid methyl ether as colorless oil.

606 mg of the thus obtained 2-hepten-4-ynyl compound is dissolved in 5 ml of methanol, 26 mg of sodium borohydride is added under ice cooling and stirring, and the mixture is stirred under ice cooling for 30 minutes. Water and methylene chloride are added to the reaction solution to form two liquid phases, the organic layer is taken and post-treated in a conventional manner, and the product is purified by silica gel column chromatography [Wako gel C-100, 20 g; hexane/ethyl acetate=4/1] to obtain 603 mg of (E,E)-3-hydroxy-2-(6,6-dimethyl-2-hepten-4-ynyl)-8-[3-(3-thienyl)phenyl]-7-octenoic acid methyl ether as colorless oil.

603 mg of the thus obtained alcohol compound is dissolved in 7 ml of methylene chloride, 279 μl of triethylamine and 124 μl of methanesulfonyl chloride are added under ice cooling and stirring, and the mixture is stirred under ice cooling for 1 hour. Water and methylene chloride are added to the reaction solution to form two liquid phases, the organic layer is washed successively with 5% hydrochloric acid, saturated aqueous sodium bicarbonate solution and saturated saline and dried over anhydrous magnesium sulfate, and then the solvent is distilled off under reduced pressure. The residue is dissolved again in 10 ml of methylene chloride, 0.3 ml of 1,8-diazabicyclo[5.4.0]-7-undecene is added, and the mixture is stirred at room temperature overnight. The reaction solution is neutralized with acetic acid, water and methylene chloride are added to form two liquid phases, the organic layer is taken and post-treated in a conventional manner, and the product is purified by silica gel column chromatography [Wako gel C-200, 50 g; hexane/ethyl acetate=9/1] to obtain 271 mg of the captioned compound as colorless oil.

(E,E)-2-(6,6-dimethyl-2-hepten-4-ynyl)-7-[3-(3-thienyl)phenoxy]-2-heptenoic acid methyl ester is obtained by carrying out the same reactions as in Referential Example 1 except that 5-[3-(3-thienyl)phenoxy]valeronitrile [synthesized by condensing 3-(3-thienyl)phenol with 5-bromovaleronitrile in dimethylformamide in the presence of sodium hydride] is used in place of (E)-6-[3-(3-thienyl)phenyl]-5-hexenenitrile which is the raw material compound used in the above.

REFERENTIAL EXAMPLE 2

Preparation of (E,E,E)-2-(6,6-dimethyl-2-hepten-4-ynyl)-3-[3-[2-[3-(3-thienyl)phenyl]ethenyl]phenyl]acrylic acid ethyl ester 3.34 g of diethylphosphonoacetic acid ethyl ester is dissolved in 40 ml of ethanol, 594 mg of 60% oily sodium hydride is added under ice cooling and stirring, and ethanol solution (10 ml) of 600 mg of (E)-6,6-dimethyl-2-hepten-4-ynyl bromide is added dropwise, and the mixture is stirred for 5 hours. The reaction solution is neutralized with 1N hydrochloric acid and then concentrated under reduced pressure, the residue is dissolved in a mixture of water with ethyl acetate, the organic layer is taken and post-treated in a conventional manner, and the product is purified by silica gel column chromatography [Wako gel C-200, 140 g; hexane/ethyl acetate=3/1→1/1] to obtain 686 mg of (E)-diethylphosphono-(6,6-dimethyl-2-hepten-4-ynyl)acetic acid ethyl ester as colorless oil.

483 mg of the thus obtained phosphonate and 409 mg of (E)-3-[2-[3-(3-thienyl)phenyl]ethenyl]benzaldehyde are dissolved in 10 ml of tetrahydrofuran, 56 mg of 60% oily sodium hydride is added under ice cooling and stirring, the mixture is stirred under ice cooling for 30 minutes, 10 ml of dimethylformamide is added, and the mixture is stirred for further 30 minutes. Water and ethyl ether are added to the reaction solution to form two liquid phases, the organic layer is taken and post-treated in a conventional manner, and the product is treated with a small amount of silica gel and then purified by medium pressure liquid chromatography [Lobar column, size B, Lichroprep Si 60F (produced by Merck Co.); hexane→hexane/ethyl acetate=15/1] to obtain 402 mg of the captioned compound as colorless oil.

(E,E)-2-(6,6-dimethyl-2-hepten-4-ynyl)-4-[2-[3-(3-thienyl)phenoxy]ethoxy]crotonic acid ethyl ester, (E,E)-2-(6,6-dimethyl-2-hepten-4-ynyl)-3-[3-[3-(3-thienyl)phenoxymethyl]phenyl]acrylic acid ethyl ester, (E,E)-2-(6,6-dimethyl-2-hepten-4-ynyl)-3-[4-(3-thienyl)-2-thienylmethoxy]phenyl]acrylic acid ethyl ester and (E,E,E)-2-(6,6-dimethyl-2-hepten-4-ynyl)-3-[5-[3-(3-thienyl)-2-propenyloxymethyl]-2-furyl]acrylic acid ethyl ester are obtained, respectively, by carrying the same reactions as in Referential Example 2 except that corresponding aldehyde derivatives are used in place of (E)-3-[2-[3-(3-thienyl)phenyl]ethenyl]benzaldehyde which is the raw material compound used in the above.

REFERENTIAL EXAMPLE 3

Preparation of (E,E,E)-2-(6-methoxy-6-methyl-2-hepten-4-ynyl)-3-[3-[2-[3-(3-thienyl)phenyl]ethenyl]phenyl]acrylic acid ethyl ester 3.36 g of diethylphosphonoacetic acid ethyl ester is dissolved in 40 ml of ethanol, 0.60 g of 60% oily sodium hydride is added under ice cooling and stirring, 1.09 g of (E)-6-methoxy-6-methyl-2-hepten-4-ynyl bromide is added dropwise, and the mixture is stirred under ice cooling for 1 hour and then at room temperature for 5 hours. 15 ml of acetic acid is added to the reaction solution, the solvent is distilled off under reduced pressure, and the residue is extracted with a system of water and ethyl acetate. The organic layer is post-treated in a conventional manner, and the product is purified by silica gel column chromatography [Wako gel C-200, 100 g; hexane/ethyl acetate=½] and medium pressure liquid chromatography [Lobar column, size B, Lichroprep Si 60F (produced by Merck Co.); hexane/ethyl acetate=1/1→½] to obtain 1.01 g of (E)-diethylphosphono(6-methoxy-6-methyl-2-hepten-4-ynyl)acetic acid ethyl ester as colorless oil.

378 mg of the thus obtained phosphonate and 291 mg of (E)-3-[2-[3-(3-thienyl)phenyl]ethenyl]benzaldehyde are dissolved in 7 ml of tetrahydrofuran, 40 mg of 60% oily sodium hydride is added under ice cooling and stirring, the mixture is stirred under ice cooling for 30 minutes and then at room temperature for 1 hour. Water and ethyl ether are added to the reaction solution to form two liquid phases, the organic layer is post-treated in a conventional manner, and the product is purified by silica gel column chromatography [Wako gel C-100, 20 g; hexane/ethyl acetate=4/1] to obtain 454 mg of the captioned compound as colorless oil.

(E,E)-2-(6,6-dimethyl-2-hepten-4-ynyl)-3-[3-[2-[3-(3-thienyl)phenyl]ethyl]phenyl]acrylic acid ethyl ester and (E,E)-2-(6-methoxy-6-methyl-2,4-heptadiynyl)-3-[3-[2-[3-(3-thienyl)phenyl]ethenyl]phenyl]acrylic acid ethyl ester are obtained by carrying out the same reactions as in Referential Example 3 except that (E)-6,6-dimethyl-2-hepten-4-ynyl bromide or 6-methoxy-6-methyl-2,4-heptadiynyl bromide and/or 3-[2-[3-(3-thienyl)phenyl]ethyl]benzaldehyde are used, respectively, in place of (E)-6-methoxy-6-methyl-2-hepten-4-ynyl bromide and/or (E)-3-[2-[3-(3-thienyl)phenyl]ethenyl]benzaldehyde which are the raw material compounds used in the above.

REFERENTIAL EXAMPLE 4

Preparation of (E)-2-(6,6-dimethyl-2-hepten-4-ynyl)-3-[3-[3-(3-thienyl)phenylmethoxy]phenyl]propionic acid methyl ester 4.05 ml of malonic acid dimethyl ester is dissolved in 40 ml of dimethylformamide, 1.29 g of 60% oily sodium hydride and 6.5 g of (E)-6,6-dimethyl-2-hepten-4-ynyl bromide (containing about 5% Z-form) are added gradually, and the mixture is stirred at that temperature for 1 hour. Saturated saline and ethyl ether are added to the reaction solution to form two liquid phases, the ether layer is taken, washed with saturated saline and dried over anhydrous magnesium sulfate, and the solvent is distilled off under reduced pressure. The residue is purified by silica gel column chromatography [Wako gel C-200, 400 g; hexane/ethyl acetate=19/1→9/1] to obtain 6.26 g of (E)-6,6-dimethyl-2-hepten-4-ynylmalonic acid dimethyl ester as colorless oil.

3.2 g of the thus obtained monoalkyl compound is dissolved in 60 ml of ethanol, 30 ml of 4N aqueous sodium hydroxide solution is added, and the mixture is refluxed with heating for 2 hours. The reaction solution is concentrated under reduced pressure, the residue is 0 dissolved in a mixture of saturated saline with ethyl acetate, and 6N hydrochloric acid is added to make the solution acidic (pH 1). The organic layer is taken, washed with saturated saline and dried over anhydrous magnesium sulfate, and the solvent is distilled off under reduced pressure. The residue is dissolved in 30 ml of xylene, the solution is heated at 150° C. for 2 hours, and the solvent is distilled off again under reduced pressure. The residue is purified by silica gel column chromatography [Wako gel C-200, 100 g; methylene chloride→methylene chloride/methanol=50/1] and methyl-esterified using an ethyl ether solution of diazomethane to obtain 1.85 g of (E)-8,8-dimethyl-4-nonen-6-ynoic acid as light yellow oil.

427 mg of the thus obtained ester compound, 790 mg of 3-[3-(3-bromomethylphenoxymethyl)phenyl]thiophene and 1.52 ml of hexamethylphosphoric triamide (HMPA) are dissolved in 22 ml of tetrahydrofuran, 2.2 ml of a 1M tetrahydrofuran solution of lithium hexamethyldisilazane ([Me$_3$Si]$_2$NLi) is added under cooling at $-78°$ C. and stirring, and the mixture is stirred at that temperature for 30 minutes. Saturated saline and ethyl ether are added to the reaction solution to form two liquid phases, the organic layer is taken and post-treated in a conventional manner, and the product is purified by silica gel column chromatography [Wako gel C-200, 60 g; hexane/ethyl acetate=30/1→20/1] to obtain 727 mg of the captioned compound as a colorless oil.

(E,E)-2-(6,6-dimethyl-2-hepten-4-ynyl)-3-[3-[2-[3-(3-thienyl)phenyl]ethenyl]phenyl]propionic acid methyl ester, (E)-2-(6,6-dimethyl-2-hepten-4-ynyl)-3-[3-[4-(3-thienyl)-2-thienylmethoxy]phenyl]propionic acid methyl ester, (E)-2-(6,6-dimethyl-2,4-heptadiynyl)-3-[3-[2-[3-(3-thienyl)phenyl]ethenyl]phenyl]propionic acid methyl ester, (E)-2-(6,6-dimethyl-2-hepten-4-ynyl)-7-[3-(3-thienyl)phenoxy]heptanoic acid methyl ester and (E,E)-2-(6,6-dimethyl-2-hexen-4-ynyl)-8-[3-(3-thienyl)phenyl]-7-octenoic acid methyl ester are obtained by carrying out the same reactions as in Referential Example 4 except that 6,6-dimethyl-2,4-heptadiynyl bromide and/or (E)-3-[3-[2-[3-(3-bromomethylphenyl)ethenyl]phenyl]thiophene, 2-(3-bromomethylphenoxymethyl)-4-(3-thienyl)thiophene, 3-[3-(5-iodopentanoxy)phenyl]thiophene or (E)-3-[3-(6-iodo-1-hexenyl)phenyl]thiophene are used, respectively, in place of (E)-6,6-dimethyl-2-hepten-4-ynyl bromide and/or 3-[3-(3-bromomethylphenoxymethyl)phenyl]thiophene which are the raw material compounds used in the above reaction.

REFERENTIAL EXAMPLE 5

Preparation of 2-[3-(3-thienyl)phenoxy]ethoxyacetaldehyde

A methylene chloride solution (2 ml) of 126 mg of 2-[2-[3-(3-thienyl)phenoxy]ethoxy]ethanol is added to a mixed solution of 352 mg of pyridinium chlorochromate, 274 mg of sodium acetate, 130 mg of molecular sieves (4A) and 5 ml of methylene chloride, the mixture is stirred at room temperature for 1.5 hours, the reaction solution is diluted with ethyl ether, silica gel is added, and the insoluble matters are removed by filtration. The filtrate is concentrated under reduced pressure, and the residue is purified by silica gel column chromatography [Wako gel C-200, 10 g; hexane/ethyl acetate=4/1→2/1] to obtain 45 mg of the captioned compound as colorless oil.

REFERENTIAL EXAMPLE 6

Preparation of 3-[2-[3-(3-thienyl)phenyl]ethyl]benzaldehyde 1.88 g of 3-(3-thienyl)benzaldehyde and 5.9 g of 3-methoxycarbonylphenyl(triphenyl)phosphonium bromide are added to a mixture of 60 ml of tetrahydrofuran and 6 ml of dimethylformamide, 0.48 g of 60% oily sodium hydride is added under ice cooling and stirring, and the mixture is stirred at room temperature for 6 hours. The reaction solution is neutralized with acetic acid, the solvent is distilled off under reduced pressure, and the residue is extracted with a system of water and methylene chloride. The organic layer is post-treated in a conventional manner, and the product is purified by silica gel column chromatography [Wako gel C-200, 60 g; hexane/ethyl acetate=10/1] to obtain 1.24 g (Z)-3-[2-[3-(3-thienyl)phenyl]ethenyl]benzoic acid methyl ester as a white crystalline solid.

1.24 g of the thus obtained ethenyl compound is added to a mixture of 12 ml of acetic acid with 12 ml of ethyl acetate, and reduction is carried out in the presence of 0.24 g of 10% palladium-carbon catalyst under a hydrogen pressure of 4 kg/cm² for 24 hours. The catalyst is removed by filtration, the solvent is distilled off under reduced pressure, and the residue is purified by silica gel column chromatography [Wako gel C-200, 60 g; hexane/methylene chloride=10/1→3/1] and medium pressure liquid chromatography [Lobar column, size B, Lichroprep Si 60F (produced by Merck Co.); hexane/ethyl acetate=50/1→20/1] to obtain 0.79 g of 3-[2-[3-(3-thienyl)phenyl]ethyl]benzoic acid methyl ester as colorless oil.

0.78 of the thus obtained ester compound is dissolved in 10 ml of ethyl ether, 0.16 g of lithium aluminum hydride is added under ice cooling and stirring, and the mixture is stirred at that temperature for 1 hour. Saturated saline is added to the reaction solution to decompose the excessive reducing agent, the mixture is neutralized with 1N hydrochloric acid, and then ethyl ether and water are added for extraction. The organic layer is taken and post-treated in a conventional manner to obtain 0.69 g of 3-[2-[3-(3-thienyl)phenyl]ethyl]benzyl alcohol as white crystalline powder.

0.38 of the thus obtained alcohol compound is dissolved in 15 ml of methylene chloride, 1.5 g of active manganese dioxide is added, and the mixture is stirred at room temperature for 6 hours. The precipitate is removed by filtration, the filtrate is evaporated under reduced pressure, and the residue is purified by silica gel column chromatography [Wako gel C-200, 20 g; hexane/methylene=1/1] to obtain 0.35 g of the captioned compound as colorless oil.

REFERENTIAL EXAMPLE 7

Preparation of (E)-3-[3-(6-iodo-1-hexenyl)phenyl]thiophene 44.6 g of 4-cyanobutyl(triphenyl)phosphonium bromide is suspended in 250 ml of dimethylformamide, 4.2 g of 60% oily sodium hydride is added under ice cooling and stirring, the mixture is stirred at that temperature for 30 minutes, 18 g of 3-(3-thienyl)benzaldehyde is added, and the mixture is stirred at room temperature for 20 hours. Water and acetic acid are added to the reaction solution for neutralization, the solvent is distilled off under reduced pressure, and the residue is post-treated in a conventional manner and purified by silica gel column chromatography [Wako gel C-100, 500 g; hexane/ethyl acetate=5/1] to obtain 23.2 g of (E)-3-[3-(5-cyano-1-pentenyl)phenyl]thiophene as colorless oil.

1.9 g of the thus obtained cyano compound is dissolved in 40 ml of methylene chloride, 22 ml of 1M toluene solution of diisobutylaluminum hydride is added under ice cooling at −78° C. and stirring, and the mixture is stirred at that temperature for 2 hours. Saturated saline and methylene chloride are added to the reaction solution to form two liquid phases, and the organic layer is taken and dried over anhydrous magnesium sulfate. The desiccating agent is removed by filtration, the solvent is distilled off under reduced pressure, the residue is dissolved in 30 ml of methanol, 0.3 g of sodium borohydride is added, and the mixture is stirred at room temperature for 1 hour. The reaction solution is concentrated to dryness under reduced pressure, the residue is extracted with a system of water and ethyl acetate, the organic layer is post-treated in a conventional manner, and the resultant product is purified by silica gel column chromatography [Wako gel C-200, 50 g; hexane/ethyl acetate=7/1] to obtain 1.82 g of (E)-6-[3-(3-thienyl)phenyl]-5-hexen-1-ol as colorless oil.

1.72 of the thus obtained alcohol compound is dissolved in 30 ml of ethyl acetate, 1 ml of triethylamine and 0.7 ml of methanesulfonyl chloride are added, and the mixture is stirred at that temperature for 30 minutes. Saturated saline is added to the reaction solution, the mixture is stirred at room temperature for 15 minutes, the organic layer is taken and dried over anhydrous magnesium sulfate, and the solvent is distilled off under reduced pressure. The residue is dissolved in a mixture of 30 ml of dimethylformamide with 10 ml of water, 5.0 g of potassium iodide is added, and the mixture is stirred with heating at 90° C. for 3 hours. The reaction solution is concentrated under reduced pressure, the residue is extracted with a system of water and ethyl ether, the organic layer is post-treated in a conventional manner, and the product is purified by silica gel column chromatography [Wako gel C-200, 100 g; hexane/ethyl acetate=20/1] to obtain 2.27 g of captioned compound as colorless oil.

INDUSTRIAL APPLICABILITY

The compounds of this invention inhibit the biosynthesis of cholesterol and lower the cholesterol levels in the blood by inhibiting the squalene epoxidases of mammals. Therefore, these compounds are expected to be effective as an agent for treatment and prophylaxis of diseases caused by excess of cholesterol, for example obesity, hyperlipidemia and arteriosclerosis and cardiac and encephalic diseases accompanying them, etc.

We claim:

1. A substituted heterocyclic derivative having squalene epoxidase inhibiting activity and represented by the following formula (I)

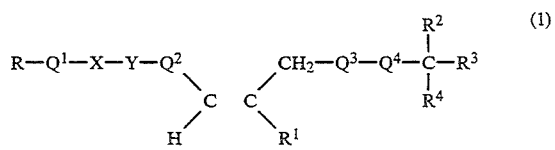

wherein

R represents a thienyl group;

$Q^1$ represents a divalent group selected from the group consisting of

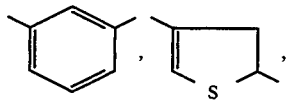

—CH=CH—CH$_2$—, —CH$_2$—CH=CH—, —CH$_2$—O—CH$_2$—, and trimethylene;

X and Y, are the same or different, and represent methylene group, oxygen atom or sulfur atom; or X and Y combine to form a vinylene group or ethylene group;

$Q^2$ represents (a) phenyl or furyl; or (b) a group represented by the formula —F—G—I—, where Z, G, and I are the same or different, and each represents an oxygen atom, a sulfur atom, a methylene group or a group represented by the formula —CH=;

$R^1$ represents a lower alkyl group, a lower alkenyl group, a lower hydroxyalkyl group, a lower alkoxy-alkyl group, a lower alkanoyloxyalkyl group or a lower alkylthioalkyl group; ... denotes a single bond or double bond provided that in the case of the single bond it is a group formed by addition of two hydrogen atoms to the corresponding double bond; $Q^3$ denotes an ethylene group, a vinylene group or an ethynylene group; $Q^4$ denotes a vinylene group or an ethynylene group; $R^2$ and $R^3$ are the same or different and denote lower alkyl groups, or they combine to denote a group forming a cycloalkane together with the adjacent carbon atom; and $R^4$ denotes a hydrogen atom, a lower alkyl group or a lower alkoxy group.

2. The substituted heterocyclic derivative according to claim 1 wherein $Q^2$ represents

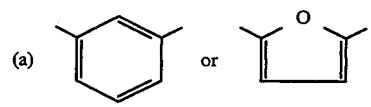

3. The substituted heterocyclic derivative according to claim 1 wherein $Q^2$ represents (b) —CH$_2$=CH—CH$_2$—, —CH$_2$—CH=CH—, —CH$_2$—O—CH$_2$— or a trimethylene group.

4. The substituted heterocyclic derivative according to claim 1 wherein R is a 3-thienyl group.

5. The substituted heterocyclic derivative according to claim 1 wherein $R^1$ is a methyl group, an ethyl group, a propyl group, a vinyl group, a 1-propenyl group, an allyl group, a hydroxymethyl group, a methoxymethyl group, an ethoxymethyl group, an acetoxymethyl group, a methylthiomethyl group or an ethylthiomethyl group.

6. The substituted heterocyclic derivative according to claim 1 wherein $R^2$ and $R^3$ are the same or different, and each are a methyl group or an ethyl group or they combine together with the adjacent carbon atom to form a cyclopropane ring.

7. The substituted heterocyclic derivative according to claim 1 wherein $R^4$ is a hydrogen atom, a methyl group, an ethyl group, a propyl group, a methoxy group or an ethoxy group.

8. A pharmaceutical composition effective for treatment or prophylaxis of hypercholesterolemia, hyperlipidemia, or arteriosclerosis which comprises a substituted heterocyclic derivative having squalene epoxidase inhibiting activity according to claim 1 and a pharmaceutically effective carrier.

9. A method for the treatment or prophylaxis of hypercholesterolemia, hyperlipidemia, or arteriosclerosis which comprises administering to a patient in need thereof a pharmacologically effective amount of a substituted heterocyclic derivative as defined in claim 1.

10. (E)-3-[3-[3-(2-methoxymethyl-8,8-dimethyl-4-nonen-6-ynyl)phenoxymethyl]phenyl]thiophene.

* * * * *